US008841254B2

(12) United States Patent
Tregear et al.

(10) Patent No.: US 8,841,254 B2
(45) Date of Patent: Sep. 23, 2014

(54) METHOD FOR TREATMENT OF ANXIETY

(75) Inventors: Geoffrey Tregear, Hawthorn (AU); Ross Alexander David Bathgate, Brunswick West (AU); Chrishan Surendran Samuel, Glen Waverley (AU); Tanya Christine Burazin, Macleod (AU); Andrew Lawrence Gundlach, Hawthorn (AU); John Desmond Wade, Canterbury (AU)

(73) Assignee: Howard Florey Institute of Experimental Physiology and Medicine, Parkville (AU)

( * ) Notice: Subject to any disclaimer, the term of this patent is extended or adjusted under 35 U.S.C. 154(b) by 796 days.

(21) Appl. No.: 11/892,215

(22) Filed: Aug. 21, 2007

(65) Prior Publication Data

US 2008/0176795 A1 Jul. 24, 2008

Related U.S. Application Data

(62) Division of application No. 10/491,919, filed as application No. PCT/AU02/01338 on Oct. 2, 2002, now abandoned.

(30) Foreign Application Priority Data

Oct. 8, 2001 (AU) ...................................... PR8144

(51) Int. Cl.
*A61K 38/22* (2006.01)
*C07K 2/00* (2006.01)

(52) U.S. Cl.
USPC .......................... 514/12.7; 514/17.5; 530/300

(58) Field of Classification Search
None
See application file for complete search history.

(56) References Cited

U.S. PATENT DOCUMENTS

| 5,753,623 | A | 5/1998 | Amento et al. |
| 7,049,403 | B2 | 5/2006 | Itoh et al. |
| 2002/0012967 | A1 | 1/2002 | Holloway et al. |
| 2006/0073567 | A1 | 4/2006 | Itoh et al. |

FOREIGN PATENT DOCUMENTS

| EP | 1283260 | 2/2003 |
| JP | 6-510045 A | 10/1994 |
| JP | 11-512072 A | 10/1999 |
| JP | 2001-12310 A | 8/2001 |
| WO | 93-37555 A2 | 4/1993 |
| WO | 96-40186 | 12/1996 |
| WO | WO 01/68862 | 9/2001 |

OTHER PUBLICATIONS

Hossain, Chem Biol Drug Des. 2009; 73: 46-62.*
van der Westhuizen et al., Drug Discovery Today, 2008; 13: 640-651.*
Hossain et al., JBC, 2008; 283: 17287-17297.*
Borsini et al., Psychopharmacology, 2002; 163: 121-141.*
Tonks, BMJ, 2003; 326: 700-702.*
Smith et al., Ann. N.Y. Acad. Sci. 2009; 1160: 236-241.*
Ryan et al., Behavioural Brain Research, 2013; 244: 142-151.*
Gavino et al, BioDrugs, 15(9):609-614 (2001).
Bathgate et al, J. of Biological Chemistry, 277(2):1148-1157 (2002).
Park et al, Rev. Endocr. Metab. Disord., 6:291-296 (2005).
RA Agarwal et al., "Alterations in brain 5-hydroxytryptamine metabolism during the 'withdrawal' phase after chronic treatment with diazepam and bromazepam", Br. J. Pharmacol., 1977, 60(1): 3-9.
Ross A. Bathgate et al., "International Union of Pharmacology LVII: Recommendations for the Nomenclature of Receptors for Relaxin Family Peptides", Pharmacological Reviews, 2006, 58(1): 7-31.
Ross A.D. Bathgate et al., "Relaxin-3: Improved Synthesis Strategy and Demonstration of Its High-Affinity Interaction with the Relaxin Receptor LGR7 Both In Vitro and In Vivo", Biochemistry, 2006, 45: 1043-1053.
Michael R. Bruchas et al., "CRF1-R Activation of the Dynorphin/Kappa Opioid System in the Mouse Basolateral Amygdala Mediates Anxiety-Like Behavior", PLoS One, 2009, 4(12): 1-9.
Tanya C.D. Burazin et al., "Restricted, but abundant, expression of the novel rat gene-3 (R3) relaxin in the dorsal tegmental region of brain", Journal of Neurochemistry, 2002, 82: 1553-1557.
MG Craske et al., "What is Anxiety Disorder?", Depress Anxiety, 2009, 26(12): 1066-1085.
Anne Dekeyne et al., "Behavioural Models for the Characterisation of Established and Innovative Antidepressant Agents", Therapie, 2005, 60(5): 477-484.
Linda M. Haugaard-Jonsson et al., "Structure of the R3/I5 Chimeric Relaxin Peptide, a Selective GPCR135 and GPCR142 Agonist", The Journal of Biological Chemistry, 2008, 283(35): 23811-23818.
Richard L. Hauger et al., "Role of CRF Receptor Signaling in Stress Vulnerability, Anxiety, and Depression", Annual NY Acad. Sci., 2009, 1179: 120-143.
Y. Ida et al., "Attenuating effect of diazepam on stress-induced increases in noradrenaline turnover in specific brain regions of rats: antagonism by Ro 15-1788", Life Sci., 1985, 37(26): 2491-2498.
M. Imamura et al., "Modulation of GABA-gated chloride ion influx in the brain by dehydroepiandrosterone and its metabolites", Biochem. Biophys. Res. Commun., 1998, 243(3): 771-775.
HP Jedema et al., "Corticotropin-releasing hormone directly activates noradrenergic neurons of the locus ceruleus recorded in vitro", J. Neurosci., 2004, 24(43): 9703-9713.

(Continued)

Primary Examiner — Christina Borgeest
(74) Attorney, Agent, or Firm — Sughrue Mion, PLLC

(57) ABSTRACT

Human H3 preprorelaxin, human H3 prorelaxin, human H3 relaxin, human relaxin analogues having a modified A chain and/or a modified B chain are described. Also described are nucleic acid sequences encoded human H3 preprorelaxin, human H3 prorelaxin, human H3 relaxin, human relaxin analogues. Also described are methods for the treatment of conditions responsive to administration of H3 relaxin or analogues thereof.

32 Claims, 6 Drawing Sheets

(56) References Cited

OTHER PUBLICATIONS

JH Kehne et al., "Therapeutic utility of non-peptidic CRF1 receptor antagonists in anxiety, depression, and sress-related disorders: evidence from animal models", Pharmacol. Ther., 2010, 128(3):460-487.

Chester Kuei et al., "R3(BΔ23-27)R/I5 Chimeric Peptide, a Selective Antagonist for GPCR135 and GPCR142 over Relaxin Receptor LGR7: In Vitro and In Vivo Characterization", The Journal of Biological Chemistry, 2007, 282(35): 25425-25435.

Changlu Liu et al., "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7", Molecular Pharmacology, 2005, 67(1): 231-240.

S. Ma et al., "Relaxin-3 in Gaba Projection Neurons of Nucleus Incertus Suggests Widespread Influence on Forebrain Circuits via G-Protein-Coupled Receptor-135 in the Rat", Neuroscience, 2007, 144: 165-190.

AK Mehta et al., "Characterization of a benzodiazepine receptor site with exceptionally high affinity for Ro 15-4513 in the rat CNS", Brain Res., 1995, 704(2): 289-297.

C. Mombereau et al., "Differential effects of acute and repeated citalopram in mouse models of anxiety and depression", Int. J. Neuropsychopharmacology, 2010, 13(3): 321-334.

EM Mueller et al., "The type IV phosphodiesterase inhibitor rolipram disturbs expression and extinction of conditioned fear in mice", Neuropharmacology, 2010, 59(1-2): 1-8.

EA Myers et al., "The anxiogenic drug yohimbine activates central viscerosensory circuits in rats", J. Comp. Neurol., 2005, 492(4): 426-441.

S. Pellow et al., "Validation of open: closed arm entries in a elevated plus-maze as a measure of anxiety in the rat", Journal of Neuroscience Methods, 1985, 14(3): 149-167.

S. Rotzinger et al., "Behavioral effects of neuropeptides in rodent models of depression and anxiety", Peptides, 2010, 31(4): 736-756.

LM Shin et al., "The neurocircuitry of fear, stress, and anxiety disorders", Neuropsychopharmacology, 2010, 35(1): 169-191.

Kelly S. Sink et al., "Calcitonin Gene-Related Peptide in the Bed Nucleus of the Stria Terminalis Produces an Anxiety-Like Pattern of Behavior and Increases Neural Activation in Anxiety-Related Structures", The Journal of Neuroscience, 2011, 31(5): 1802-1810.

Craig M. Smith et al., "Distribution of Relaxin-3 and RXFP3 Within Arousal, Stress, Affective, and Cognitive Circuits of Mouse Brain", The Journal of Comparative Neurology, 2010, 518: 4016-4045.

Steven W. Sutton et al., "Distribution of G-Protein-Coupled Receptor (GPCR)135 Binding Sites and Receptor mRNA in the Rat Brain Suggests a Role for Relaxin-3 in Neuroendocrine and Sensory Processing", Neuroendocrinology, 2004, 80: 298-307.

Y. Sztainberg et al., "The anxiolytic effect of environmental enrichment is mediated via amygdalar CRF receptor type 1", Molecular Psychiatry, 2010, 15: 905-917.

Lorey K. Takahashi, "Role of $CRF_1$ and $CRF_2$ receptors in fear and anxiety", Neuroscience & Biobehavioral Reviews, 2001, 25(7-8):627-636.

Carol A. Tamminga (Ed.), "The Anatomy of Fear Extinction", American Journal of Psychiatry, 2006, 163(6): 961.

VM Tanay et al., "Common effects of chronically administered antipanic drugs on brainstem GABA(A) receptor subunit gene expression", Mol. Psychiatry, 2001, 6(4): 404-412.

O. Valverde et al., "Modulation of anxiety-like behavior and morphine dependence in CREB-deficient mice", Neuropsychopharmacology, 2004, 29(6): 1122-1133.

Huaibo Zhang et al., "Neuropeptide Y Signaling in the Central Nucleus of Amygdala Regulates Alcohol-Drinking and Anxiety-Like Behaviors of Alcohol-Preferring Rats", Alcohol Clin. Exp. Res., 2010, 34(3): 451-461.

\* cited by examiner

Fig. 1A

A: H3 relaxin assembled gene sequence

TATAAATGGGGGGCCAAGAGGCAGCAGAGACACTGGCCCACTCTCACGTTCAAAGCGTCT

CCGTCCAGCATGGCCAGGTACATGCTGCTGCTGCTCCTGGCGGTATGGGTGCTGACCGGG
         M  A  R  Y  M  L  L  L  L  A  V  W  V  L  T  G
                   ←——— Signal peptide ———

GAGCTGTGGCCGGGAGCTGAGGCCCGGGCAGCGCCTTACGGGGTCAGGCTTTGCGGCCGA
 E  L  W  P  G  A  E  A  |R  A  A  P  Y  G  V  R  L  C  G  R|

GAATTCATCCGAGCAGTCATCTTCACCTGCGGGGGCTCCCGGTGGAGACGATCAGACATC
 |E  F  I  R  A  V  I  F  T  C  G  G  S  R  W|  R  R  S  D  I
              | B Chain |

CTGGCCCACGAGGCTATGG>>gtgaggctggggagagagtggatgtagaaggggaacag-
 L  A  H  E  A  M

——————————————————intron 2318bp——————————————————
-cactaactctgttcatcttttgcag<<GAGATACCTTCCCGGATGCAGATGCTGATGAA
                             G  D  T  F  P  D  A  D  A  D  E GACAGTCTGGCAGGCGAGCTGGATGAGGCCATGGGGTCCAGCGAGTGGCTGGCCCTGACC
 D  S  L  A  G  E  L  D  E  A  M  G  S  S  E  W  L  A  L  T
                    ——— C Chain ———

AAGTCACCCCAGGCCTTTTACAGGGGGCGACCCAGCTGGCAAGGAACCCCTGGGGTTCTT
 K  S  P  Q  A  F  Y  R  G  R  P  S  W  Q  G  T  P  G  V  L

CGGGGCAGCCGAGATGTCCTGGCTGGCCTTTCCAGCAGCTGCTGCAAGTGGGGGTGTAGC
 R  G  S  R |D  V  L  A  G  L  S  S  C  C  K  W  G  C  S|
                          | A Chain |

AAAAGTGAAATCAGTAGCCTTTGCTAGTTTGAGGGCTGGGCAGCCGTGGGCACCAGGACC
 |K  S  E  I  S  S  L  C|  * (SEQ ID NO:53)

AATGCCCCAGTCCTGCCATCCACTCAACTAGTGTCTGGCTGGGCACCTGTCTTTCGAGCC
TCACACATTCATTCATTCATCTACAAGTCACAGAGGCACTGTGGGCTCAGGCACAGTCTC
CCGACACCACCTATCCAACCCTGCCCTTTGACCAGCCTATCATGACCCTGGCCCCTAAGG
AAGCTGTGCCCCTGCCTGGTCAAGTGGGGACCCCCCCATCCTGACCCCTGACCTCTCCCC
AGCCCTAACCATGCGTTTGCCTGGCCTACACACTCCACTGCCACAACTGGGTCCCTACTC
TACCTAGGCTGGCCACACAGAGACCCCTGCCCCCTTCCCAGTCCAAACTGTGGCCATTGT
CCCCTGACCAGCTAAAATCAAGCCTCTGTCTCAGTCCAGCCTTTGCACGCACGCTTCCTT
TGCCCTGCTTTCCATCCCCTCTCCCTCCAACTCCCCTGCCAGAGTTCCAAGGCTGTGGAC
CCCAGAGAAGGTGGCAGGTGGCCCCCCTAGGAGAGCTCTGGGCACATTCGAATCTTCCCA
AACTCCAATAATAAAAATTCGAAGACTTTGGCAGAGAGTGTGTGTGTGTGTGTATGGTTG (SEQ ID NO:52)

Fig. 1B

B: M3 relaxin assembled gene sequence

```
TATAAATAGGGGATCGGAGGTGGTGCAGATAGAGCACCTGGGTCGCAGGCATCTCAACTG

ATCATGGCAATGCTCGGGCTGCTGCTGCTGGCTTCCTGGGCTCTCCTCGGGGCTCTGGGG
   M  A  M  L  G  L  L  L  L  A  S  W  A  L  L  G  A  L  G
           ◄─────────── signal peptide ───────────
CTGCAGGCCGAGGCGAGGCCGGCGCCCTACGGGGTGAAGCTCTGCGGTCGGGAGTTCATC
 L  Q  A  E  A │R  P  A  P  Y  G  V  K  L  C  G │R│ E  F  I │
              ──►   ◄──                          ─────────────
                         │ B chain │
CGCGCGGTCATCTTCACTTGCGGAGGCTCACGATGGCGCCGGGCGGACATCTTGGCCCAC
│R│ A  V │I│ F  T  C  G  G  S  R │ R  R  A  D  I  L  A  H
 ────────────────────────────────►   ◄──
GAATCTCTGG>>gtgagtgctaggcaatcaacctggaacaggtgtcctggtaagcgcaa-
  E  S  L
 ─────────
---------------------intron 1446b---------------------
-cttttgcag>>>GGGACTTCTTCGCTGATGGAGAAGCCAATACAGACCACCTGGCCAGC
            G  D  F  F  A  D  G  E  A  N  T  D  H  L  A  S GAGCTGGATGAAGCGGTGGGCTCCAGCGAGTGGCTGGCCCTAACCAAATCCCCCCAGGCT
 E  L  D  E  A  V  G  S  S  E  W  L  A  L  T  K  S  P  Q  A
                          ───────── C chain ─────────
TTCTACGGTGGTCGAGCCAGCTGGCAAGGGTCACCTGGAGTGGTTCGGGGCAGCAGAGAT
 F  Y  G  G  R  A  S  W  Q  G  S  P  G  V  V  R  G  S  R │D│
                                                    ──────►◄─
GTGTTGGCTGGCCTTTCCAGCAGTTGCTGCGAGTGGGGCTGTAGCAAGAGCCAAATTAGC
│V  L  A  G  L  S  S  S  C  C  E  W  G  C  S  K  S  Q  I  S
                                        │ A chain │
AGCTTGTGCTAGGATCAGGGTTGAGCAATGGAGAAGCGGGCCGTGCCTGCAAGCTGCTGT
│S  L  C │ *  (SEQ ID NO:55)
 ─────────►
CAGCTGTGCGATGTTCAAGAGCATTCCTACAGGCGAGGCACCAAGGGGTCCACTGTCTCC
TTACAGACCCTCTGCCAAGATGCACACACTACGTGCCAACCTTTCCCCACCTTGCTGCCG
GCCCCTCCTCTATCCAGCCAAACAGAAACTTGTTTTTCATGACTGAGTTCTTCCGTGCCA
CAACCTCACCCCCAGCAGCCCAGCAGCAACCAGATGCCCATCTTCTTAAACTGGCTACAC
TAGAGTCTGCCCCACCTCCACCCTCAGTCCGGCCCTAATTGCCGCCACTGTCCCTGGCTA
ACCTGCCCCCCCCCAAAAAAAAAAAAACAGAGCACTCTGTTGCAGACCCCAGGACTGAG
GGCCCCTGGTCCTCAGTACTCAGACTTCCTCACCACATAAAATAAAGGTTCAGTTCTGAG (SEQ ID NO:54)
```

B Chain Aligns

```
                 1    5    10   15   20   25
Human 1          KWKDDVIKLCGRELVRAQIAICGMSTWS   (SEQ ID NO:34)
Human 2          DSWMEEVIKLCGRELVRAQIAICGMSTWS  (SEQ ID NO:35)
Cons 1,2,3       ......++LCGRE.+RA.I..CG.S.W.
Human 3          RAAPYGVRLCGREFIRAVIFTCGGSRW    (SEQ ID NO:56)
Cons 3           R.APYGV+LCGREFIRAVIFTCGGSRW
Mouse 3          RPAPYGVKLCGREFIRAVIFTCGGSRW    (SEQ ID NO:40)
Cons Mouse       ......+++CGRE+.R.+I..CG.S..
Mouse 1          RVSEEWMDGFIRMCGREYARELIKICGASVGRLAL  (SEQ ID NO:42)
```

A Chain Aligns

```
                 1    5    10   15   20
Human 1          RPYVALFEKCCLIGCTKRSLAKYC    (SEQ ID NO:43)
Human 2          QLYSALANKCCHVGCTKRSLARFC    (SEQ ID NO:44)
Cons 1,2,3       ...+.L...CC..GC+K..++..C
Human 3          DVLAGLSSSCCKWGCSKSEISSLC    (SEQ ID NO:57)
Cons 3           DVLAGLSSSCC+WGCSKS+ISSLC
Rat 3            DVLAGLSSSCCEWGCSKSQISSLC    (SEQ ID NO:49)
Mouse 3          DVLAGLSSSCCEWGCSKSQISSLC    (SEQ ID NO:50)
Cons Mouse       +....+S..CC..GCS+..I..L-C
Mouse 1          ESGGLMSQQCCHVGCSRRSIAKLYC   (SEQ ID NO:51)
```

Fig. 3
A.
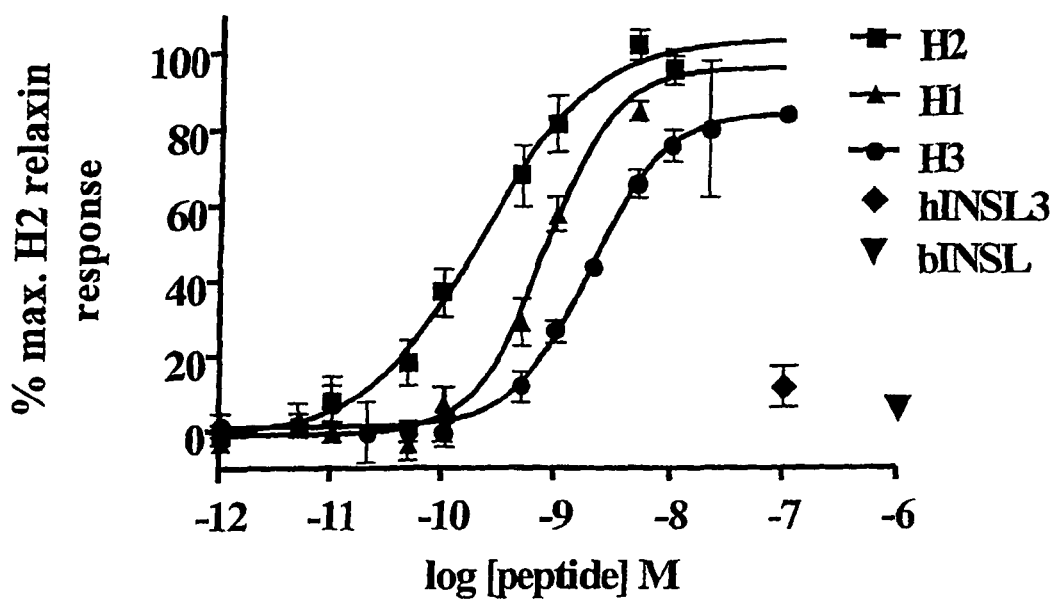
B.
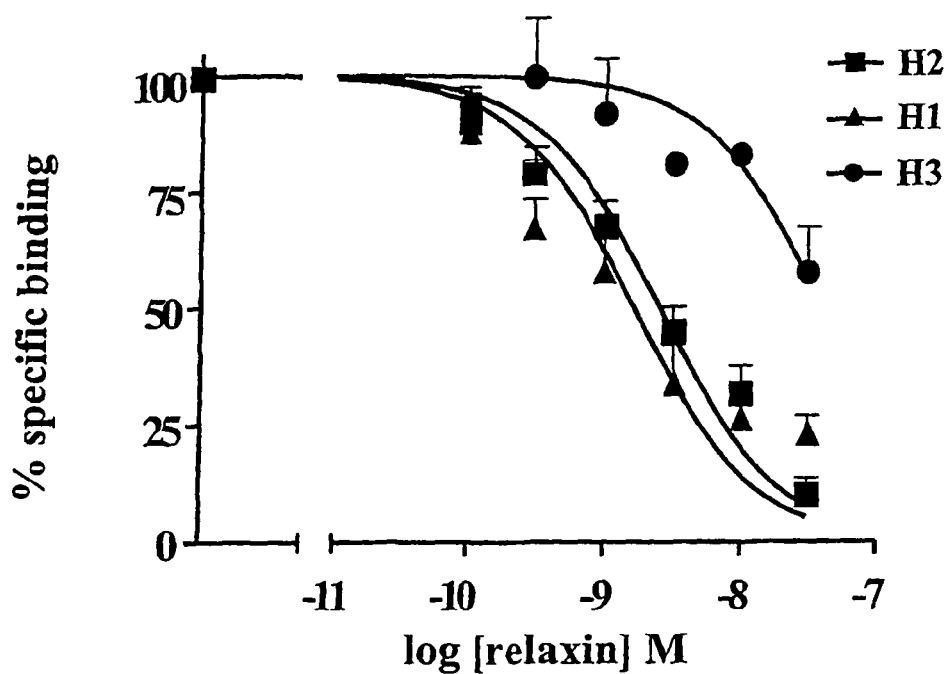

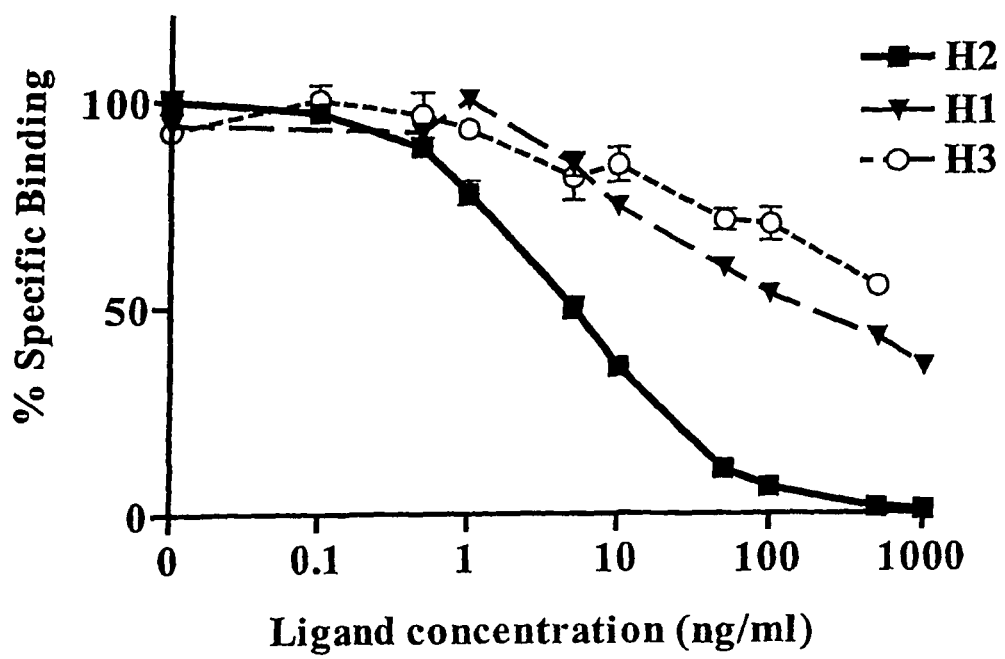

METHOD FOR TREATMENT OF ANXIETY

CROSS-REFERENCE TO RELATED APPLICATIONS

This Application is a Divisional of U.S. application Ser. No. 10/491,919, filed Sep. 29, 2004; which is a 371 of PCT/AU02/01338, filed Oct. 2, 2002, the disclosure of each of which is incorporated herein by reference.

FIELD OF THE INVENTION

This invention relates to human 3 relaxin (hereafter referred to as "H3 relaxin"). More specifically, the invention relates to H3 relaxin, pro- and prepro-H3 relaxin, the individual peptide chains which comprise these sequences, analogues of H3 relaxin, compositions including pharmaceutical compositions, as well as therapeutic uses and methods of treatment. Further, the invention relates to nucleic acids encoding H3 relaxin, H3 pro- and prepro-relaxin, H3 relaxin analogues, and individual peptide chains which comprise these sequences.

BACKGROUND OF THE INVENTION

Pioneering work by Hisaw 1926 first suggested an important role for the peptide hormone relaxin in animals through its effect in dilating the pubic symphsis, thus facilitating the birth process. Relaxin is synthesised in the corpora lutea of ovaries during pregnancy, and is released into the blood stream prior to parturition. The availability of ovarian tissue has enabled the isolation and amino acid sequence determination of relaxin from the pig (James et al (1977), *Nature*, 267, 554-546), the rat (John et al (1981) *Endocrinology*, 108, 726-729), and the shark (Schwabe et al (1982) *Ann. N.Y. Acad. Sci.*, 380, 6-12).

Relaxin genes and the encoded relaxin polypeptides have been identified in many species including man, pig, rat, sheep and shark. In all these species only one relaxin gene has been characterised in mammals, with the exception of the human and higher primates where two separate genes have been described. The separate human genes were identified by the present applicant and designated H1 (Hudson et al (1983) *Nature*, 301, 628-631) and H2 (Hudson et al (1984) *Embo. J.*, 3, 2333-2339).

The peptide encoded by the H2 gene is the major stored and circulating form in the human (Winslow et al (1992) *Endrocrinology*, 130, 2660-2668). H1 relaxin expression is restricted to the decidua, placenta and prostate (Hansell et al (1991) *J. Clin. Endocrinol. Metab.*, 72, 899-904), however, the H1 peptide has similar biological activity to that of H2 relaxin in a rat atrial bioassay (Tan et al (1998) *Br. J. Pharmacol* 123, 762-770).

The actions of relaxin include an ability to inhibit myometrial contractions, to stimulate remodelling of connective tissue and to induce softening of the tissues of the birth canal. Additionally, relaxin increases growth and differentiation of the mammary gland and nipple and induces the breakdown of collagen, one of the main components of connective tissue. Relaxin decreases collagen synthesis and increases the release of collagenases (Unemori et al (1990) *J. Biol. Chem.* 265, 10682-10685). These findings were recently confirmed by the establishment of the relaxin gene-knockout mouse (Zhao et al (1999) *Endocrinology* 140, 445-453), which exhibited a number of phenotypic properties associated with pregnancy. Female mice lacking a functionally active relaxin gene failed to relax and elongate the interpubic ligament of the pubic symphysis and could not suckle their pups, which in turn, died within 24 hours unless cross-fostered to relaxin wildtype or relaxin heterozygous foster mothers.

Evidence has accumulated to suggest that relaxin is more than a hormone of pregnancy and acts on cells and tissues other than those of the female reproductive system. Relaxin causes a widening of blood vessels (vasodilatation) in the kidney, mesocaecum, lung and peripheral vasculature, which leads to increased blood flow or perfusion rates in these tissues (Bani et al (1997) *Gen. Pharmacol* 28, 13-22). It also stimulates an increase in heart rate and coronary blood flow, and increases both glomerular filtration rate and renal plasma flow (Bani et al (1997) *Gen. Pharmacol.* 28, 13-22). The brain is another target tissue for relaxin where the peptide has been shown to bind to receptors (Osheroff et al (1991) *Proc. Nal. Acad. Sci. U.S.A.* 88, 6413-6417; Tan et al (1999) *Br. J. Pharmacol* 127, 91-98) in the circumventricular organs to affect blood pressure and drinking (Parry et al (1990) *J Neurodendocrinol* 2, 53-58; Summerlee et al (1998) *Endocrinology* 139, 2322-2328; Sinnahay et al (1999) *Endocrinology* 140, 5082-5086).

Important clinical uses arise for relaxin in various diseases responding to vasodilation, such as coronary artery disease, peripheral vascular disease, kidney disease associated with arteriosclerosis or other narrowing of kidney capillaries, or other capillaries narrowing in the body, such as in the eyes or in the peripheral digits, the mesocaecum, lung and peripheral vasculature.

The finding of two human relaxin genes, and encoded human relaxin peptide products nearly 20 years ago was of itself most surprising.

Even more surprisingly with the benefit of nearly 20 years of further research and development in relaxin biology internationally, the applicant has identified, isolated and characterised nucleic acid sequences encoding a third human relaxin gene (H3), the encoded H3 relaxin peptide and the constituent peptide chains thereof. The production of H3 relaxin and analogues thereof has been made possible, as have uses and therapeutic treatment methods.

SUMMARY OF THE INVENTION

In a first aspect the invention relates to the peptides human H3 relaxin, H3 pro relaxin and H3 preprorelaxin, to the individual peptide chains which comprise these sequences and to analogues thereof, particularly truncated and/or amino acid substituted modifications. Preferably the peptides are provided as pharmaceutically acceptable compositions for human or animal administration, by various therapeutic routes. Peptides are preferably isolated in purified or homogenous form free of contaminating peptides and proteins, or in a form of about 90-99% purity.

In a second aspect of the invention there is provided a composition comprising human H3 relaxin or a human H3 relaxin analogue having an A chain and a B chain, the A chain having the amino acid sequence:

```
                                              (SEQ ID NO: 4)
Asp Val Leu Ala Gly Leu Ser Ser Ser Cys Cys Lys
1               5                   10

Trp Gly Cys Ser Lys Ser Glu Ile Ser Ser Leu Cys
            15                  20
``` or an amino acid sequence truncated by up to about 9 amino acids from N-terminus, the B chain having the amino sequence:

```
                                             (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
            15                  20

Ser Arg Trp
25
``` or an amino acid sequence truncated by up to 9 amino acids from the amino-terminus and/or up to about 5 amino acids from the carboxyl-terminus, the A and B chains being linked by interchain disulphide bonds at A11-B10, and A24-B22, and wherein the human H3 relaxin or analogue thereof has relaxin bioactivity.

In a third aspect of the invention there is provided a composition comprising a human H3 relaxin analogue having a modified A chain and/or a modified B chain, the H3 relaxin A chain having the amino acid sequence:

```
                                             (SEQ ID NO: 4)
Asp Val Leu Ala Gly Leu Ser Ser Ser Cys Cys Lys
1               5                   10

Trp Gly Cys Ser Lys Ser Glu Ile Ser Ser Leu Cys
            15                  20
``` wherein the carboxyl-terminus is an amide derivative and/or Lys at position 12 is replaced with Glu, and/or Glu at position 19 is replaced with Gln, the H3 relaxin B chain having the amino acid sequence:

```
                                             (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
            15                  20

Ser Arg Trp
25
``` wherein the carboxyl-terminus is an amide derivative, and/or Ala at position 2 is replaced with Pro, and/or Arg at position 8 is replaced with Lys, the A and B chains being linked by disulphide bonds between A11-B10 and A24-B22 and wherein the human H3 relaxin analogue has relaxin bioactivity.

In accordance with a fourth aspect of the invention there is provided a composition comprising human H3 preprorelaxin or human H3 prorelaxin, having a signal, A chain, B chain and C chain in respect of human H3 preprorelaxin, and an A chain, B chain and C chain in respect of human H3 prorelaxin, the said amino acid chains having the amino acid sequences: the A chain comprising:

```
                                             (SEQ ID NO: 4)
Asp Val Leu Ala Gly Leu Ser Ser Ser Cys Cys Lys
1               5                   10

Trp Gly Cys Ser Lys Ser Glu Ile Ser Ser Leu Cys
            15                  20
``` the B chain comprising:

```
                                             (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
            15                  20

Ser Arg Trp
25
``` the signal sequence comprising:

```
                                             (SEQ ID NO: 1)
Met Ala Arg Tyr Met Leu Leu Leu Leu Ala Val
1               5                   10

Trp Val Leu Thr Gly Glu Leu Trp Pro Gly Ala Glu
            15                  20

Ala
25
``` and the C chain comprising:

```
                                             (SEQ ID NO: 3)
Arg Arg Ser Asp Ile Leu Ala His Glu Ala Met Gly
1               5                   10

Asp Thr Phe Pro Asp Ala Asp Ala Asp Glu Asp Ser
            15                  20

Leu Ala Gly Glu Leu Asp Glu Ala Met Gly Ser Ser
25                      30                  35

Glu Trp Leu Ala Leu Thr Lys Ser Pro Gln Ala Phe
                40                  45

Tyr Arg Gly Arg Pro Ser Trp Gln Gly Thr Pro Gly
    50                  55                  60

Val Leu Arg Gly Ser Arg
                65
```

In accordance with a fifth aspect of the invention there is provided a composition comprising the C chain of human H3 relaxin, the C chain having the amino acid sequence:

```
                                             (SEQ ID NO: 3)
Arg Arg Ser Asp Ile Leu Ala His Glu Ala Met Gly
1               5                   10

Asp Thr Phe Pro Asp Ala Asp Ala Asp Glu Asp Ser
            15                  20

Leu Ala Gly Glu Leu Asp Glu Ala Met Gly Ser Ser
25                      30                  35

Glu Trp Leu Ala Leu Thr Lys Ser Pro Gln Ala Phe
                40                  45

Tyr Arg Gly Arg Pro Ser Trp Gln Gly Thr Pro Gly
    50                  55                  60

Val Leu Arg Gly Ser Arg
                65
```

In accordance with a sixth aspect of the invention there is provided a nucleic acid sequence encoding human prepro-H3 relaxin comprising the nucleic acid sequence:

```
                                                          (SEQ ID NO: 6)
tataaatggg gggccaagag gcagcagaga cactggccca ctctcacgtt caaagcgtct    60
ccgtccagca tggccaggta catgctgctg ctgctcctgg cggtatgggt gctgaccggg   120
gagctgtggc cgggagctga ggcccgggca gcgccttacg gggtcaggct ttgcggccga   180
gaattcatcc gagcagtcat cttcacctgc ggggctccc ggtggagacg atcagacatc   240
ctggcccacg aggctatggg tgaggctggg gagagagtgg atgtagaagg ggaacaggtg   300
gctggatggg tcccaggagc taaggacaga gataagagga ggttgctgga ggaggagggt   360
ccctgtcctg ccacattcag ccagggacac ctgcccagcc ttgaaacaag ggctcaggag   420
ttagcagagc tgcagagctg ggatggggtg ttgcaagcca tccatggggg ctggaagtct   480
gaggacaggt gggggcgggg agcgtgccat ttgcaaagac aacaccgaag tgttttccaa   540 cccttttccag caggtaatgt gaagggtgtg gtatacacat agctgggttt gtcacctaat   600
gcatgacctc tccccagcaa gttggttttt cttccgtctc tgagtgtctt ttttttggag   660
atgtggtctc actccattgc ccaggcttga atgcagtggc ccaatcactg ctcattgcag   720
cctcgacctc ccaggctcaa gtgattctcc tgcctccgcc tccagagtag ttgagaccac   780
aggcacctga caccatgcct ggctagtttt aaatttttttt ttttgtagaaa caggggtctc   840 actatgttgc ctaggctggt ctcgaactcc tgggctcaag tgatcctccc acctcggcct   900
ccctaagtgc tgagattaga gtctctgagt gtctttatct tcaaatggga gacacagttc   960
ctgaatcttg caggattaag tggtatgatt aaatcaaaac agattagggc agagtctcag  1020
cagggcagcg gcacaatctg ggatccatca ggagagtcag agggaacaga agacctagct  1080
tcatgagggg cagggacctg gcaaatagat attcatgatg gtgagaagga ggataggtat  1140
gagcgtggac atagaagaca caccacttgg attcagatag tagctctaca atgtaatagt  1200
tgtgtgttca tgtgctacta tttttttttt ttttgagaca gaatctcatt ctgttgccca  1260
ggctggagtg cagtggtgca atcttggctc actgtaacct ccatcacctg ggttcaagcg  1320
attctcgtgc ctccagcctc ccaagtagct gggattacag atgtgtgcca ccatacctcg  1380
ctaatctttt tatttttagt agagacagtt tcaccatgtt ggccaggctg gtctccaact  1440
cctgacctca ggtgatcctc ccacctcagc ctcccaaagt gctgggatta caggcatgag  1500
ccaccgcgcc cagccatgca aattctttac tgagtcctgc ctcagtggtc tcctctggaa  1560
aatacgggtg ataactgcac ccacctcaac tggttatcac tgagaagaat aaagaagtta  1620
acctgctaaa gcacttaaaa cgttgtttga cacaaagtaa gtgatcaata aattattatt  1680
attattatta ttattattat tattattatt tttgagacag ggtcttgctc tgttgcccag  1740
actggagtgc agtggtgtga tcacagctca ctgcagcttc aacctcttgg gctcaagcaa  1800
ttctcctgcc tcagcctcct gagtagctgg gactacaggc ttgtgccaac atgtctaact  1860
ttttattatt tgtagagaca gggtagtgct gtgttgtcca ggctgttctt gaactcctgg  1920
ttctggtgat cctccagcat gtgccctgg aagtgctggg attacaggtg tgagacaccg  1980
tgcccggact caatagtcat ttttgagtgc tcatcatgtt ccagacattg ttctaagttt  2040
ttttttttaa tgaatattaa ctccttataa aacttgagaa ggttggagta attattttt  2100 tccactttgc agaaaagaac attgaggctc caagaagtaa atttacttgc tcacgattag  2160
agaagctgga ttcatgctca gtcagcccag ctcccaaatg taccaggtcc tcaattaata  2220
aagagtaagg agaaataaat gacagggctg ggtgcggtgg ctcacgcctg taatcccagc  2280
actttgggtg gctgaggtgg gcacatcact tgaggtcagg agtttgcgac cagcctgaac  2340
aacatggtga accccatctc tataacaata caaaaatcag ccaggcctgc tggcagacac  2400
```

```
ctgtaatccc acctactctg gcagagccag aatttgaacc caggactggg tggaataaaa    2460
actctgaact atgtctatga ctgttgtcac aagatcagag ctagactggc caggagccat    2520
gactgtgggt gcagcagcag ctgagccctg atcactaact ctgttcatct tttgcaggag    2580
ataccttccc ggatgcagat gctgatgaag acagtctggc aggcgagctg gatgaggcca    2640
tggggtccag cgagtggctg gccctgacca agtcacccca ggcctttttac aggggcgac     2700 ccagctggca aggaacccct ggggttcttc ggggcagccg agatgtcctg gctggccttt    2760
ccagcagctg ctgcaagtgg gggtgtagca aaagtgaaat cagtagcctt tgctagtttg    2820
agggctgggc agccgtgggc accaggacca atgccccagt cctgccatcc actcaactag    2880
tgtctggctg ggcacctgtc tttcgagcct cacacattca ttcattcatc tacaagtcac    2940
agaggcactg tgggctcagg cacagtctcc cgacaccacc tatccaaccc tgcccttga     3000 ccagcctatc atgaccctgg cccctaagga agctgtgccc ctgcctggtc aagtggggac    3060 cccccatcc tgaccctga cctctcccca gccctaacca tgcgtttgcc tggcctacac      3120
actccactgc cacaactggg tccctactct acctaggctg gccacacaga gacccctgcc    3180
cccttcccag tccaaactgt ggccattgtc ccctgaccag ctaaaatcaa gcctctgtct    3240
cagtccagcc tttgcacgca cgcttccttt gccctgcttt ccatccctc tccctccaac     3300 tcccctgcca gagttccaag gctgtggacc ccagagaagg tggcaggtgg cccccctagg    3360
agagctctgg gcacattcga atcttcccaa actccaataa taaaaattcg aagactttgg    3420
cagagagtgt gtgtgtgtgt gtatggttg                                      3449
```

In accordance with a seventh aspect of the invention there is provided a nucleic acid sequence encoding human pro-H3 relaxin including an A chain, B chain and C chain sequence, the A chain sequence comprising:

```
                                                         (SEQ ID NO: 7)
gatgtcctgg ctggcctttc cagcagctgc tgcaagtggg ggtgtagcaa aagtgaaatc   60
agtagccttt gc                                                       72
``` the B chain sequence comprising:

```
                                                         (SEQ ID NO: 8)
cgggcagcgc cttacggggt caggctttgc ggccgagaat tcatccgagc agtcatcttc   60
acctgcgggg gctcccggtg g                                             81
``` the C chain sequence comprising:

```
                                                         (SEQ ID NO: 9)
agacgatcag acatcctggc ccacgaggct atgggagata ccttcccgga tgcagatgct   60
gatgaagaca gtctggcagg cgagctggat gaggccatgg ggtccagcga gtggctggcc  120
ctgaccaagt caccccaggc cttttacagg gggcgaccca gctggcaagg aaccctggg   180 gttcttcggg gcagccga                                                198
```

In an eighth aspect of the invention there is provided a nucleic acid sequence encoding human H3 relaxin having an A and B chain, the A chain sequence comprising:

```
                                                         (SEQ ID NO: 7)
gatgtcctgg ctggcctttc cagcagctgc tgcaagtggg ggtgtagcaa aagtgaaatc   60
agtagccttt gc                                                       72
``` and the B chain sequence comprising:

```
                                                          (SEQ ID NO: 8)
cgggcagcgc cttacggggt caggcttttgc ggccgagaat tcatccgagc agtcatcttc   60
acctgcgggg gctcccggtg g                                              81
```

In a ninth aspect of the invention there is provided a nucleic acid sequence encoding the A, B or C peptide chains of human H3 relaxin, the said chains comprising the nucleic acid sequences:

A chain:

```
                                                          (SEQ ID NO: 7)
gatgtcctgg ctggcctttc cagcagctgc tgcaagtggg ggtgtagcaa aagtgaaatc   60
agtagccttt gc                                                        72
```

B chain:

```
                                                          (SEQ ID NO: 8)
cgggcagcgc cttacggggt caggcttttgc ggccgagaat tcatccgagc agtcatcttc   60
acctgcgggg gctcccggtg g                                              81
``` and C chain:

```
                                                          (SEQ ID NO: 9)
agacgatcag acatcctggc ccacgaggct atgggagata ccttcccgga tgcagatgct   60
gatgaagaca gtctggcagg cgagctggat gaggccatgg ggtccagcga gtggctggcc  120
ctgaccaagt caccccaggc cttttacagg gggcgaccca gctggcaagg aaccccctggg 180 gttcttcggg gcagccga                                                198
```

The nucleic acid sequences are isolated and purified nucleic acids, and may be contained within a vector, such as a plasmid, bacteriophage or virus DNA or RNA, and may be in single or double stranded form, and may include promoters or enhancers or other sequences which confer elevated, enhanced or other effects on expression in a host-system such as a bacterial cell.

The triplet codons of nucleic acids encode specific amino acids. More than one codon may encode the same amino acid, as is well and established in the art. Moreover, methods of modifying or altering the sequence of nucleic acids are well known in the art. Insofar as this invention pertains in its various aspects to nucleic acids encoding human H3 relaxin, pro-H3 relaxin, prepro-H3 relaxin, and constituent peptide chains thereof, the invention includes nucleic acid variants which encode the same protein products, or a protein product having relaxin activity.

Nucleotide sequence aspects of this invention also include closely related nucleic acid sequences as defined by stringent hybridization, this being annealing of complimentary sequences under conditions of 0.25M $H_2PO_4$, pH 7.2, 1 mmol EDTA, 20% SDS at 65° C. overnight; followed by 3 washes for 5 min in 2×SSC, 0.1% SDS at room temperature; and finally a 30 min wash at 65° C. in 0.1% SSC; where 6×SSC is 0.9M NaCl, 0.3M $Na_3CO_2H_2O$ at ph 7.0. Such sequences will encode H3 relaxin polypeptides having biological or immunological or other activity corresponding to those of H3 relaxin.

In another aspect of the invention there is provided a method for the treatment of one or more of: vascular disease including coronary artery disease, peripheral vascular disease, vasospasm including Raynaud's phenomenon, microvascular disease involving the central and peripheral nervous system, kidney, eye and other organs; treatment of arterial hypertension; diseases related to uncontrolled or abnormal collagen or fibronectin formation such as fibrotic disorders (including fibrosis of lung, heart and cardiovascular system, kidney and genitourinary tract, gastrointestinal system, cutaneous, rheumatologic and hepatobiliary systems); kidney disease associated with vascular disease, interstitial fibrosis, glomerulosclerosis, or other kidney disorders; psychiatric disorders including anxiety states including panic attack, agoraphobia, global anxiety, phobic states; depression or depressive disorders including major depression, dysthymia, bipolar and unipolar depression; neurologic or neurodegenerative diseases (including memory loss or other memory disorders, dementias, Alzheimer's disease); disorders of learning, attention and motivation (including Attention Deficit Hyperactivity Disorder, Tourette's disease, impulsivity, antisocial and personality disorders, negative symptoms of psychoses including those due to schizophrenia, acquired brain damage and frontal lobe lesions); addictive disorders (including drug, alcohol and nicotine addiction); movement and locomotor disorders (including Parkinson's disease, Huntington's disease, and motor deficits after stoke, head injury, surgery, tumour or spinal cord injury); immunological disorders (including immune deficiency states, haematological and reticuloendothelial malignancy; breast disorders (including fibrocystic disease, impaired lactation, and cancer); endometrial disorders including infertility due to impaired implantation; endocrine disorders (including adrenal, ovarian and testicular disorders related to steroid or peptide hormone production); delayed onset of labour, impaired cervical ripening, and prevention of prolonged labour due to fetal dystocia; sinus bradycardia; hair loss, alopecia; disorders of water balance including impaired or inappropriate secretion of vasopressin; placental insufficiency; which comprises administering to a subject in need of any such treatments a therapeutically effective amount of human H3 relaxin, or an analogue thereof as herein defined, optionally in association with one or more pharmaceutically acceptable carriers and/diluents and/or excipients.

In another aspect of the invention there is provided use of human H3 relaxin or an analogue thereof in the manufacture of medicaments for the treatment of one or more of: vascular disease including coronary artery disease, peripheral vascular disease, vasospasm including Raynaud's phenomenon, microvascular disease involving the central and peripheral nervous system, kidney, eye and other organs; treatment of arterial hypertension; diseases related to uncontrolled or abnormal collagen or fibronectin formation such as fibrotic disorders (including fibrosis of lung, heart and cardiovascular system, kidney and genitourinary tract, gastrointestinal system, cutaneous, rheumatologic and hepatobiliary systems); kidney disease associated with vascular disease, interstitial fibrosis, glomerulosclerosis, or other kidney disorders; psychiatric disorders including anxiety states including panic attack, agoraphobia, global anxiety, phobic states; depression or depressive disorders including major depression, dysthymia, bipolar and unipolar depression; neurologic or neurodegenerative diseases (including memory loss or other memory disorders, dementias, Alzheimer's disease); disorders of learning, attention and motivation (including Attention Deficit Hyperactivity Disorder, Tourette's disease, impulsivity, antisocial and personality disorders, negative symptoms of psychoses including those due to schizophrenia, acquired brain damage and frontal lobe lesions); addictive disorders (including drug, alcohol and nicotine addiction); movement and locomotor disorders (including Parkinson's disease, Huntington's disease, and motor deficits after stoke, head injury, surgery, tumour or spinal cord injury); immunological disorders (including immune deficiency states, haematological and reticuloendothelial malignancy; breast disorders (including fibrocystic disease, impaired lactation, and cancer); endometrial disorders including infertility due to impaired implantation; endocrine disorders (including adrenal, ovarian and testicular disorders related to steroid or peptide hormone production); delayed onset of labour, impaired cervical ripening, and prevention of prolonged labour due to fetal dystocia; sinus bradycardia; hair loss, alopecia; disorders of water balance including impaired or inappropriate secretion of vasopressin; placental insufficiency; which comprises administering to a subject in need of any such treatments a therapeutically effective amount of human H3 relaxin, or an analogue thereof as herein defined, optionally in association with one or more pharmaceutically acceptable carriers and/diluents and/or excipients.

| Sequence Listing Table | |
| --- | --- |
| SEQ ID NO: 1 | Signal peptide sequence |
| SEQ ID NO: 2 | B chain peptide sequence |
| SEQ ID NO: 3 | C chain peptide sequence |
| SEQ ID NO: 4 | A chain peptide sequence |
| SEQ ID NO: 6 | Genomic DNA sequence |
| SEQ ID NO: 7 | A chain nucleic acid sequence |

| Sequence Listing Table | |
| --- | --- |
| SEQ ID NO: 8 | B chain nucleic acid sequence |
| SEQ ID NO: 9 | C chain nucleic acid sequence |

DESCRIPTION OF THE FIGURES

FIGS. 1A-1B. Assembled DNA sequence of the H3 (A) (SEQ ID NO:52) and M3 (B) (SEQ ID NO:54) genes and proteins (SEQ ID NOs:53 and 55), respectively.

Figure 2B:
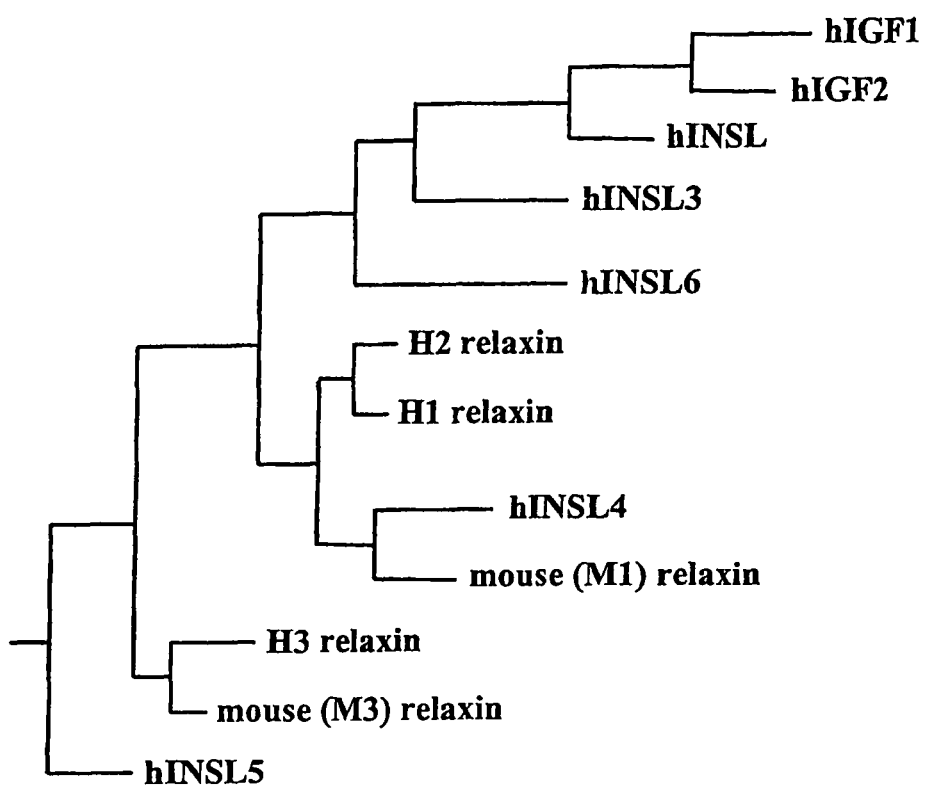

Start and Stop codons as well as predicted TATA boxes and polyadenylation sequences are underlined. The positions of the putative signal peptide, and B-, C- and A-chain peptide sequences are indicated by arrows. A- and B-chain sequences are boxed and the residues implicated in relaxin receptor binding are shaded. The intron sequence, which is at an identical position in the C-chain in both the human (A) and mouse (B) sequences, is indicated by lower case letters and the exact size of the intron is marked.

FIGS. 2A-2B. Sequence comparisons of H3 and M3 relaxin with other relaxin and insulin family members.

Alignments of A- and B-chain sequences from H3 and M3 relaxin with other human and mouse relaxin sequences (A). The consensus sequences are boxed; Cons 1,2,3: Consensus sequence between human relaxins 1, 2 and 3. Cons 3: Consensus sequence between H3 and M3 relaxin for the B-chain and H3, R3 and M3 relaxin for the A-chain. Cons Mouse. Consensus sequence between M1 and M3 relaxin. The rat sequence is derived from an EST clone (see results for details). "+" Denotes a conservative substitution, "." denotes no homology. Phylogenetic tree of evolution of H3 and M3 relaxin full-length sequences with human sequences of the relaxin/insulin/IGF superfamily (B).

FIGS. 3A-3B. Bioactivity of H3 compared to H1 and H2 relaxin in a human relaxin receptor expressing cell line.

cAMP accumulation in THP-1 cells upon stimulation with peptides (A). Data are expressed as mean±SEM of the maximum response (%) to H2 relaxin (n=3). The response to bovine insulin (bINSL) and human INSL3 (hINSL3) are also shown to highlight the specificity of the assay. H1, H2, H3; Human 1, 2 and 3 relaxin respectively. The ability of H1 (n=7), H2 (n=11) and H3 (n=3) relaxin peptides to compete for $^{33}$P-labeled H2 relaxin (B33) binding to THP-1 cells (B). Data are expressed as mean±SEM of the specific binding (%).

FIG. 4. Ability of a well characterized H2 relaxin antibody to recognize H3 relaxin.

The H2 relaxin antibody was immobilized onto ELISA plates and a competition experiment was performed using H1, H2 and H3 relaxin against $^{125}$I-labeled H2 relaxin. Results are mean±SEM of the specific binding (%) of triplicate determinations from a representative assay.

Unexpectedly, some 20 years after the identification of human relaxin, and the surprising identification at that time of two human relaxin genes, a further relaxin gene has been identified. This invention in its various aspects provides: the characterisation of nucleotide sequences encoding human H3 relaxin; the isolation of purified nucleic acid material; amplification of nucleotide sequences encoding H3 relaxin (mRNA, cDNA and DNA); nucleic acid cloning of H3 relaxin sequences; nucleic acid sequence identification, and peptide sequences encoding human H3 preprorelaxin, H3 prorelaxin and H3 relaxin.

The human H3 relaxin polypeptide comprises disulphide bridged A and B chains. The amino acid sequence of human H3 relaxin is set out in SEQ ID NO: 4. The amino acid sequence of the B chain of human relaxin is set out in SEQ ID NO: 2.

The A and B chains of human H3 relaxin are linked through cysteine residues, A11-B10, A24-B22 disulphide bond formation taking place between these cysteine linkages.

Hence, the amino acid sequence of human H3 relaxin A and B chains are as follows:

A Chain

```
                                          (SEQ ID NO: 4)
Asp Val Leu Ala Gly Leu Ser Ser Cys Cys Lys
1               5                   10

Trp Gly Cys Ser Lys Ser Glu Ile Ser Ser Leu Cys
        15                  20
```

B Chain

```
                                          (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
        15                  20

Ser Arg Trp
25
``` the A and B chains being linked by disulphide bonds between A11-B10, A24-B22.

Human H3 relaxin possesses classical relaxin bioactivity. Human relaxins, H1 and H2 relaxin, bind to cells expressing relaxin receptors, such as THP-1 cells (Parsell et al (1996) *J. Biol. Chem.* 271, 27936-27941). H2 relaxin produces a dose dependent increase in cAMP production from these cells. Synthetic H3 relaxin produced according to this invention stimulated a dose dependent increase in cAMP in keeping with human H2 relaxin. The specificity of response in target cells bearing the human relaxin receptor as exhibited by H3 relaxin is demonstrated by the inability of bovine insulin (bINSL) or human insulin (hINSL3) to stimulate cAMP responses at doses up to 1 um in THP-1 cells.

The elicitation of a second messenger response (cAMP) by stimulating human relaxin receptors with human H3 relaxin, provides definitive evidence that human H3 relaxin has classic relaxin biological activity. Such assays in cells containing relaxin receptors, for example THP-1 cells as referred to above provides, a ready way to determine relaxin activity. In addition, the ability of human H3 relaxin to compete with $P^{32}$-labelled H2 relaxin in binding to relaxin binding sites in cells expressing relaxin receptors, again provides definitive confirmation of relaxin activity.

Other biological activities/assays for determining relaxin activity are known in the art. For example, bioassays used for the measurement of active relaxin during pregnancy and non-pregnancy, such as the guinea pig interpubic ligament assay may be used (Steinetz et al (1960) *Endocrinology* 67, 102-115, and Sirosi et al (1983) *American Journal of Obstetrics and Gynaecology* 145: 402-405) may be used. Other bioassays include cAMP production in THP-1 cells (Parsell et al (1996) J. Biol. Chem. 271, 27936-27941).

Applicant has found that H3 relaxin analogues may be prepared where up to 9 amino acids are truncated from the N-terminus of the A chain, and up to 9 amino acids are truncated from the N-terminus of the B chain, and up to 5 amino acids are truncated from the C-terminus of the B chain.

The resulting relaxin analogues comprise a H3 relaxin A and B chain, the A chain having the amino acid sequence

```
                                          (SEQ ID NO: 4)
Asp Val Leu Ala Gly Leu Ser Ser Cys Cys Lys
1               5                   10

Trp Gly Cys Ser Lys Ser Glu Ile Ser Ser Leu Cys
        15                  20
``` truncated by up to about 9 amino acids from amino-terminus, and the B chain having the amino acid sequence:

```
                                          (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
        15                  20

Ser Arg Trp
25
``` truncated by up to 9 amino acids from the amino-terminus and/or up to about 5 amino acids from the carboxyl-terminus, the A and B chains being linked by disulphide bonds between A11-B10 and A24-B22, and wherein the human H3 relaxin or analogue thereof has relaxin bioactivity. The A chain of human H3 relaxin contains an intrachain disulphide bond between Cys residues 10 and 15.

In standard assays looking at second messenger elicitation in cells bearing human relaxin receptors, the H3 relaxin analogues referred to above all elicited cyclic AMP production in a manner which was characteristic of full length, non-truncated human H3 relaxin, and indeed human H2 relaxin. Hence, such truncated H3 relaxin analogues possess relaxin bioactivity.

Another aspect of the present invention relates to compositions comprising a human H3 relaxin analogue having a modified A chain and/or a modified B chain. The carboxyl-terminus of the A chain, and/or the B chain, may be an amide derivative. Lys at position 12 in the A chain may be replaced with Glu, and/or Glu at position 19 may be replaced with Gln. In the B chain, the Ala at position 2 may be replaced with Pro, and/or Arg at position 8 may be replaced with Lys. The resulting H3 relaxin analogues having modified amino acids comprise an amino acid sequence which may be depicted as follows:

In accordance with another aspect of the invention, there is provided a human H3 relaxin analogue having a modified A chain and/or a modified B chain, the H3 relaxin A chain having the amino acid sequence:

```
                                          (SEQ ID NO: 4)
Asp Val Leu Ala Gly Leu Ser Ser Cys Cys Lys
1               5                   10

Trp Gly Cys Ser Lys Ser Glu Ile Ser Ser Leu Cys
        15                  20
``` wherein the carboxyl-terminus is an amide derivative and/or Lys at position 12 is replaced with Glu, and/or Glu at position 19 is replaced with Gln, the modified B chain having the amino acid sequence:

```
                                           (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
            15              20

Ser Arg Trp
25
``` wherein the carboxyl-terminus is an amide derivative, and/or Ala at position 2 is replaced with Pro, and/or Arg at position 8 is replaced with Lys,
the A and B chains being linked by disulphide bonds between A11-B10 and A24-B22, and wherein the human H3 relaxin analogue has relaxin bioactivity.

The isolation, purification and characterisation of nucleic acid sequences encoding human H3 relaxin has allowed the characterisation and production of the signal sequence of human H3 relaxin, and the pro-sequence of human H3 relaxin.

The identification, purification and characterisation of the signal sequence and C chain of human H3 relaxin enables the prepro- and pro-human H3 relaxin to be produced.

In accordance with another aspect of the invention there is provided a composition comprising human H3 preprorelaxin or human H3 prorelaxin, having a signal, A chain, B chain and C chain in respect of human H3 preprorelaxin, and an A chain, B chain and C chain in respect of human H3 prorelaxin, the said amino acid chains having the amino acid sequences:
the A chain comprising:

```
                                           (SEQ ID NO: 4)
Asp Val Leu Ala Gly Leu Ser Ser Cys Cys Lys
1               5                   10

Trp Gly Cys Ser Lys Ser Glu Ile Ser Ser Leu Cys
            15              20
``` the B chain comprising:

```
                                           (SEQ ID NO: 2)
Arg Ala Ala Pro Tyr Gly Val Arg Leu Cys Gly Arg
1               5                   10

Glu Phe Ile Arg Ala Val Ile Phe Thr Cys Gly Gly
            15              20

Ser Arg Trp
25
``` the signal sequence comprising:

```
                                           (SEQ ID NO: 1)
Met Ala Arg Tyr Met Leu Leu Leu Leu Ala Val
1               5                   10

Trp Val Leu Thr Gly Glu Leu Trp Pro Gly Ala Glu
            15              20

Ala
25
``` and the C chain comprising:

```
                                           (SEQ ID NO: 3)
Arg Arg Ser Asp Ile Leu Ala His Glu Ala Met Gly
1               5                   10
```

```
                    -continued
Asp Thr Phe Pro Asp Ala Asp Ala Asp Glu Asp Ser
            15                  20

Leu Ala Gly Glu Leu Asp Glu Ala Met Gly Ser Ser
25                      30                  35

Glu Trp Leu Ala Leu Thr Lys Ser Pro Gln Ala Phe
                40                  45

Tyr Arg Gly Arg Pro Ser Trp Gln Gly Thr Pro Gly
    51                  55                  60

Val Leu Arg Gly Ser Arg
                65
```

In accordance with a further aspect of the invention there is provided the C chain of human H3 relaxin, said C chain having the amino acid sequence:

```
                                           (SEQ ID NO: 3)
Arg Arg Ser Asp Ile Leu Ala His Glu Ala Met Gly
1               5                   10

Asp Thr Phe Pro Asp Ala Asp Ala Asp Glu Asp Ser
            15                  20

Leu Ala Gly Glu Leu Asp Glu Ala Met Gly Ser Ser
25                      30                  35

Glu Trp Leu Ala Leu Thr Lys Ser Pro Gln Ala Phe
                40                  45

Tyr Arg Gly Arg Pro Ser Trp Gln Gly Thr Pro Gly
    51                  55                  60

Val Leu Arg Gly Ser Arg
                65
```

Human H3 prorelaxin possesses characteristic relaxin bioactivity.

Human H3 relaxin, prorelaxin, preprorelaxin and constitutive peptide chains may be products using techniques previously described as useful in the production of relaxin such as U.S. Pat. No. 5,991,997, U.S. Pat. No. 4,758,516, U.S. Pat. No. 4,871,670, U.S. Pat. No. 4,835,251, PCT/US90/02085, and PCT/US94/0699.

Relaxin analogues and derivatives where amino acids are substituted as indicated above may be produced recombinantly using, for example, site directed mutagenesis techniques as set forth, for example, in Tsurushita et al (1988) *Gene Tissue:* 135-139.

The disclosed sequence information for human H3 relaxin, analogues thereof wherein one or more amino acids are truncated from the N- and/or C-terminus of the A and/or B chains, or human H3 relaxin analogues having amino acid substitutions as referred to above, may be synthesised according to the methods of Büllesbach (1991) *J. Biol. Chem.* 266, 10754-10761, for synthesising relaxin. Additionally, well known methods of peptide synthesis may be utilised to produce the various H3 relaxin forms referred to herein.

Relaxin has been implicated consequently in the treatment and diagnosis of various diseases and disorders. For example, studies provide evidence that relaxin is effective in the treatment of scleroderma, sinus bradycardia, cardiovascular disease, neurodegenerative and neurologic disorders, hair loss, depression. See e.g., U.S. Pat. No. 5,166,191 and International Patent Application No. PCT/US92/069). Evidence also suggests the use of relaxin in diseases and disorders related to the abnormal expression of collagen or fibronectin, such as rheumatoid arthritis.

Human H3 relaxin, human H3 relaxin truncated analogues, amino acid modified H3 relaxin analogues, and human prorelaxin provided by the instant invention bind to the relaxin receptor and possess relaxin biological activity. It directly follows that these human H3 relaxin forms possessing relaxin biological activity may be used for the treatment of the above-identified diseases and other diseases.

In accordance with another aspect of the present invention there is provided a method for the treatment of one or more of: vascular disease including coronary artery disease, peripheral vascular disease, vasospasm including Raynaud's phenomenon, microvascular disease involving the central and peripheral nervous system, kidney, eye and other organs; treatment of arterial hypertension; diseases related to uncontrolled or abnormal collagen or fibronectin formation such as fibrotic disorders (including fibrosis of lung, heart and cardiovascular system, kidney and genitourinary tract, gastrointestinal system, cutaneous, rheumatologic and hepatobiliary systems); kidney disease associated with vascular disease, interstitial fibrosis, glomerulosclerosis, or other kidney disorders; psychiatric disorders including anxiety states including panic attack, agoraphobia, global anxiety, phobic states; depression or depressive disorders including major depression, dysthymia, bipolar and unipolar depression; neurologic or neurodegenerative diseases (including memory loss or other memory disorders, dementias, Alzheimer's disease); disorders of learning, attention and motivation (including Attention Deficit Hyperactivity Disorder, Tourette's disease, impulsivity, antisocial and personality disorders, negative symptoms of psychoses including those due to schizophrenia, acquired brain damage and frontal lobe lesions); addictive disorders (including drug, alcohol and nicotine addiction); movement and locomotor disorders (including Parkinson's disease, Huntington's disease, and motor deficits after stoke, head injury, surgery, tumour or spinal cord injury); immunological disorders (including immune deficiency states, haematological and reticuloendothelial malignancy; breast disorders (including fibrocystic disease, impaired lactation, and cancer); endometrial disorders including infertility due to impaired implantation; endocrine disorders (including adrenal, ovarian and testicular disorders related to steroid or peptide hormone production); delayed onset of labour, impaired cervical ripening, and prevention of prolonged labour due to fetal dystocia; sinus bradycardia; hair loss, alopecia; disorders of water balance including impaired or inappropriate secretion of vasopressin; placental insufficiency; which comprises administering to a subject in need of any such treatments a therapeutically effective amount of human H3 relaxin, or an analogue thereof as herein defined, optionally in association with one or more pharmaceutically acceptable carriers and/or diluents and/or excipients.

In accordance with another aspect of the present invention there is provided use of human H3 relaxin or an analogue thereof in the manufacture of medicaments for the treatment of one or more of: vascular disease including coronary artery disease, peripheral vascular disease, vasospasm including Raynaud's phenomenon, microvascular disease involving the central and peripheral nervous system, kidney, eye and other organs; treatment of arterial hypertension; diseases related to uncontrolled or abnormal collagen or fibronectin formation such as fibrotic disorders (including fibrosis of lung, heart and cardiovascular system, kidney and genitourinary tract, gastrointestinal system, cutaneous, rheumatologic and hepatobiliary systems); kidney disease associated with vascular disease, interstitial fibrosis, glomerulosclerosis, or other kidney disorders; psychiatric disorders including anxiety states including panic attack, agoraphobia, global anxiety, phobic states; depression or depressive disorders including major depression, dysthymia, bipolar and unipolar depression; neurologic or neurodegenerative diseases (including memory loss or other memory disorders, dementias, Alzheimer's disease); disorders of learning, attention and motivation (including Attention Deficit Hyperactivity Disorder, Tourette's disease, impulsivity, antisocial and personality disorders, negative symptoms of psychoses including those due to schizophrenia, acquired brain damage and frontal lobe lesions); addictive disorders (including drug, alcohol and nicotine addiction); movement and locomotor disorders (including Parkinson's disease, Huntington's disease, and motor deficits after stoke, head injury, surgery, tumour or spinal cord injury); immunological disorders (including immune deficiency states, haematological and reticuloendothelial malignancy; breast disorders (including fibrocystic disease, impaired lactation, and cancer); endometrial disorders including infertility due to impaired implantation; endocrine disorders (including adrenal, ovarian and testicular disorders related to steroid or peptide hormone production); delayed onset of labour, impaired cervical ripening, and prevention of prolonged labour due to fetal dystocia; sinus bradycardia; hair loss, alopecia; disorders of water balance including impaired or inappropriate secretion of vasopressin; placental insufficiency; which comprises administering to a subject in need of any such treatments a therapeutically effective amount of human H3 relaxin, or an analogue thereof as herein defined, optionally in association with one or more pharmaceutically acceptable carriers and/or diluents and/or excipients.

Without wishing to be bound on mechanism of action, applicant believes that H3 relaxin may act as a neurotransmitter or neuroregulator in the brain, and other parts of the body including nerves, for example through inducing eAMP production in cells. H3 relaxin may also allow nutrient uptake by cells, or may be involved in autoregulatory presynaptic and/or conventional postsynaptic actions. Applicant further believes that H3 relaxin may also be axonally transported by nerve projections.

As defined hereinafter, H3 relaxin has surprisingly been found to be expressed in neuroanatomical region of the pars ventromedialis of the dorsal tegmental nucleus (vmDTg), which may otherwise be referred to as the nucleus incertus (Goto et al (2001) *Journal of Comparative Neurology* 438: 86-122). With the extensive pattern of efferents and afferents to and from key forebrain areas from the nucleus incertus, this region has been proposed as part of a brain stem network that may regulate behavioural activation via influences on attention, motivation, locomotion and learning (Goto et al) and may give rise to the therapeutic treatment modalities herein described. This is consistent with the abundant distribution of relaxin binding sites in cerebral cortex and other relevant brain areas (Osheroffand Phillips (1991) *Proc. Natl. Acad. Sci*. USA 88, 6413-6417; and Tan et al (1999) *Br. J. Pharmacol*. 127, 91-98).

H3 relaxin may cross the blood brain barrier, or may be treated to facilitate crossing of the blood brain barrier, by methods known in the art including use of one or more sugars or amino acids, or other substances which open the blood brain barrier or make it leaky allowing coadministered/timed administration with H3 relaxin (see for example Naito U.S. Pat. No. 6,294,520), by intranasal administration according to the methods of Frey (U.S. Pat. No. 6,313,093), for example using a lipophilic vehicle, and by methods described in PCT/WO89/10134.

H3 relaxin and anlogues as herein described may be effective in the treatment of a wide range of what may broadly be described as neurologic diseases including psychiatric disorders, disorders of learning, attention and memory, addictive disorders and movement and locomotor disorders.

H3 relaxin binds to the relaxin receptor as described hereinafter.

For convenience, human H3 relaxin, analogues of human H3 relaxin where one or more amino acids are truncated from the N- and/or C-terminus of the A and B chains of human H3 relaxin, analogues of human H3 relaxin where one or more amino acids are modified or substituted with another amino acid as described herein, and human H3 preprorelaxin shall collectively be referred to as human H3 relaxin, unless otherwise specifically indicated.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1).

Dosage amount and interval may be adjusted individually to provide serum levels of the active moiety which are sufficient to maintain the relaxin activity and effects.

Administration of H3 relaxin can be via any of the accepted modes of administration for agents that serve similar utilities, preferably by systemic administration.

While human dosage levels for treating many of the above-identified relaxin related diseases or disorders have yet to be optimized for H3 relaxin generally, a daily dose is from about 0.05 to 500.0 .mu.g/cg of body weight per day, preferably about 5.0 to 200.0 .mu.g/kg, and most preferably about 10.0 to 100.0 .mu.g/kg. Generally it is sought to obtain a serum concentration of the H3 relaxin approximating or greater than normal circulating levels of relaxin in pregnancy, i.e., 1.0 ng/ml, such as 1.0 to 20 ng/ml, preferably 1.0 to 20 ng/ml.

For administration to a 70 kg person, the dosage range would be about 7.0 .mu.g to 3.5 mg per day, preferably about 42.0 .mu.g to 2.1 mg per day, and most preferably about 84.0 to 700.0 .mu.g per day. The amount of the H3 relaxin administered will, of course, be dependent on the subject and the severity of the affliction, the manner and schedule of administration and the judgment of the prescribing physician and the biological activity of such analog or derivative. One treatment regimen can employ a higher initial dosage level (e.g., 100 to 200 .mu.g/kg/day) followed by decreasing dosages to achieve steady H3 relaxin serum concentration of about 1.0 ng/ml. Another treatment regimen, particularly postpartum depression, entails administration of an amount of H3 relaxin sufficient to attain normal pregnancy levels of relaxin (about 1.0 ng/ml) followed by gradual decreasing dosages until H3 relaxin serum levels are no longer detectable (e.g. less than about 20 picograms/ml), optionally discontinuing treatment upon reaching that dosage level.

Any pharmaceutically acceptable mode of administration can be used. H3 relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Such proteins can also be administered in sustained or controlled release dosage forms (e.g., employing a slow release bioerodable delivery system), including depot injections, osmotic pumps (such as the Alzet implant made by Alza), pills, transdermal (including electrotransport) patches, and the like, for prolonged administration at a predetermined rate, preferably in unit dosage forms suitable for single administration of precise dosages. The compositions will typically include a conventional pharmaceutical carrier or excipient and/or H3 relaxin, H3 prorelaxin, and H3 preprorelaxin or derivatives thereof. In addition, these compositions may include other active agents, carriers, adjuvants, etc.

In a preferred aspect of the invention, a sustained/controlled release H3 relaxin formulation was a selectively permeable outer barrier with a drug dispensing opening, and an inner H3 relaxin containing portion designed to deliver dosage of the H3 relaxin progressively diminishing at a predetermined rate (e.g. containing about 30 mg of H3 relaxin in a matrix for delivery of initially about 500 .mu.g per day diminishing as a rate of 10 .mu.g per day.

In another preferred aspect of the invention, a sustained/controlled release of H3 relaxin has a selectively permeable outer barrier with a drug dispensing opening, a first inner H3 containing portion designed for steady state release of H3 relaxin at a therapeutically effective daily dosage (e.g. containing about 50 mg of H3 relaxin in a matrix for continuous delivery of about 500 .mu.g per day), and a second inner H3 relaxin a portion designed to deliver a dosage of H3 relaxin progressively diminishing at a predetermined rate (e.g. containing about 3 mg of H3 relaxin in a matrix for delivery of initially about 500 .mu.g per day diminishing at a rate of 50 .mu.g per day) commencing upon exhaustion of the H3 relaxin from the first inner portion.

Generally, depending on the intended mode of administration, the pharmaceutically acceptable composition will contain about 0.1% to 90%, preferably about 0.5% to 50%, by weight of H3 relaxin, either alone or in combination with H3 relaxin, the remainder being suitable pharmaceutical excipients, carriers, etc. Actual methods of preparing such dosage forms are known, or will be apparent, to those skilled in this art; for example, see Remington's Pharmaceutical Sciences, Mack Publishing Company, Easton, Pa., 15th Edition, 1975.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Suitable routes of administration may, for example, include oral, rectal, transmucosal, or intestinal administration. Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

A more recently devised approach for parenteral administration employs the implantation of a slow-release or sustained-release system, such that a constant level of dosage is maintained. See, e.g., U.S. Pat. No. 3,710,795.

Alternately, one may administer the H3 in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

The pharmaceutical compositions of the present invention may be manufactured in a manner that is itself known, e.g., by means of conventional mixing, dissolving granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied:for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Formulations comprising human H3 relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364, 838, which discloses a method of administration for insulin that can be adapted for the administration of H3 relaxin.

H3 relaxin for treatment of such disorders such as alopecia, may also be administered topically in a formulation adapted for application to the scalp, such as a shampoo (e.g., as disclosed in U.S. Pat. No. 4,938,953, adapted according to methods known by those skilled in the art, as necessary for the inclusion of protein ingredients) or a gel (e.g., as disclosed in allowed U.S. Ser. No. 08/050,745) optionally with increased H3 relaxin concentrations to facilitate absorption.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Various aspects of the invention will be described with reference to the following non-limiting examples.

In the examples which follow rats are used as an experimental model to map H3 relaxin expression at the mRNA and protein level in the rat brain, this allowing human brain mapping. In this regard, the rat brain is a standard comparative anatomical model of the human brain (Goto et al (2001) *The Journal of Comparative Neurology* 438: 86-122).

EXAMPLE 1

Nucleotide Sequence Identification, Characterisation, Purification and Manipulation Tissue RNA/DNA Extraction and RT-PCR—

Human genomic DNA was extracted from human CL using standard protocols (Sambrook et al 1989) *In Molecular Cloning*: A Laboratory Manual, 2nd Ed., Cold Spring Harbour Laboratory Press, NY). Human CL and mouse tissues were finely diced in the presence of liquid nitrogen and immediately homogenized with RNAWiz reagent (Ambion Inc., Austin, Tex.), and the RNA extracted according to the manufacturer's instructions. Total RNA (5 μg) from each sample was used for the reverse transcription (RT) reaction, which was performed using the Superscript II RT-PCR kit (Gibco-BRL, Rockville, Md.) in a 20 μl volume according to the manufacturer's instructions. A 50 μl reaction containing 100 ng of primers and 150 ng of the cDNA template was used for all PCR reactions. Mouse tissues were screened for M3 relaxin expression using specific forward [5' TGCGGAG-GCTCACGATGGCGC 3' (SEQ ID NO:11)] and reverse [5' GACAGCAGCTTGCAGGCACGG 3' (SEQ ID NO:12)] primers, which generated a 319-bp product. Mouse relaxin (M1) expression was determined using a specific forward [5' GTGAATATGCCCGTGAATTGATC 3' (SEQ ID NO:13)] and reverse [5' AGCGTCGTATCGAAAGGCTCT 3' (SEQ ID NO:14)] primer based on the published sequence (Evans et al (1993) *J. Mol. Endocrinol*. 10, 15-23), generating a 150-bp product. Human CL cDNA was used in RT-PCR reactions with specific primers for H3 relaxin, forward 1 [5' ACGT-TCAAAGCGTCTCCGTCC 3' (SEQ ID NO:15)], forward 2 [5' CGGTGGAGACGATCAGACATC 3' (SEQ ID NO:16] and reverse [5' ATGGCAGGACTGGGGCATTGG 3' (SEQ ID NO:17)], generating products of 504- and 310-bp for forward 1/reverse and forward 2/reverse, respectively. All primer combinations we subsequently show to cross the single introns in the mouse and human relaxin sequences, respectively, so as to control for genomic DNA contamination. In all experiments GAPDH forward [5' TGATGACAT-CAAGAAGGTGG 3' (SEQ ID NO:18)] and reverse [5' TTTCTTACTCCTTGGAGGCC 3' (SEQ ID NO:19)] primers generating a product of 246-bp were used in separate PCR reactions to control for quality, and equivalent loading of the cDNA. M3 relaxin expression by RT-PCR was performed on cDNA samples extracted from at least two animals, although the results from only one representative experiment are shown. The mouse PCR reactions were completed in a Perkin Elmer Gene Amplifier using the following (touch-down) annealing temperatures: 64° C. (2 cycles), 63° C. (2 cycles), 62° C. (2 cycles), 61° C. (2 cycles), 60° C. (32 cycles). H3 relaxin expression in human CL cDNA was performed by RT-PCR at the following annealing temperatures: 60° C. (2 cycles), 59° C. (2 cycles), 58° C. (2 cycles), 57° C. (2 cycles), 56° C. (32 cycles). Aliquots of the PCR products were electrophoresed on 2% (w/v) agarose gels stained with ethidium bromide and photographed. Mouse tissue samples were transferred to Hybond NX membranes (Amersham International, Aylesbury, UK) for Southern blot analysis.

An additional PCR reaction was performed using mouse brain and ovarian cDNA using the reverse M3 primer (above) and a forward primer from in front of the ATG start codon (5' GGG TCGCAGGCATCTCAACTG 3' (SEQ ID NO:20). The resulting product contained the full H3 relaxin coding sequence. PCR was performed as above, but with the following annealing temperatures: 60° C. (2 cycles), 59° C. (2 cycles), 58° C. (2 cycles), 57° C. (2 cycles), 56° C. (32 cycles). To generate a specific H3 relaxin cDNA probe for $^{32}$P-labeling and to utilize it for subsequent probing of a human multi tissue array, RT-PCR was performed on human genomic DNA (50 ng). Specific forward (5' CGGATGCA-GATGCTGATGAAG 3' (SEQ ID NO:21) and reverse (5' GTGCCTGAGCCCACAGTGCCT 3' (SEQ ID NO:22)) primers from the exon II sequence of the H3 relaxin gene were used at the following annealing temperatures: 60° C. (2 cycles), 59° C. (2 cycles), 58° C. (2 cycles), 56° C. (2 cycles), 54° C. (32 cycles). These products as well as the mouse PCR product described above, were separated on 2% agarose gels. Bands were detected of the expected size under UV light (mouse 319-bp, 478-bp; human 374-bp), excised and eluted from the gel using the Ultraclean™ 15 DNA purification kit (Geneworks Pty Ltd, Adelaide, Australia). The bands were subsequently subcloned into the pGEM-T vector (Promega, Madison, Wis.) and multiple subclones were then sequenced on both strands using the ABI PRISM 377 automatic DNA sequencer, according to the manufacturers instructions (Applied Biosystems, Melbourne, Australia).

Southern Blot Analysis—

PCR products on membranes were hybridized against specific internal oligonucleotide primers for the M1 relaxin (5' CAAGCAGAGCTGGCTCCTCCTGGCT CAAAGC-CAATCTTC 3' (SEQ ID NO:23) and M3 relaxin (5' AATTTGGCTCTTGCTACAGCCCCACTCG-CAGCAACTGCT 3' (SEQ ID NO:24)) cDNA sequences, which had been labeled using T4 polynucleotide kinase and [γ-$^{32}$P] ATP. Hybridization was performed at 55° C. overnight in 5×SSC (1×SSC; 0.15 M NaCl, 15 mM sodium citrate, pH 7), 5×Denhardts, 1% SDS and 100 µg/ml sonicated herring sperm. Membranes were washed three times for 5 min in 2×SSC, 0.1% SDS at room temperature followed by a 30 min wash at 55° C. in 0.1×SSC, 0.1% SDS, before being exposed to BioMAX MR film (Eastman Kodak Co., Rochester, N.Y.) for 24 h at room temperature.

Northern Blot Analysis—

To further examine the expression of M3 relaxin mRNA, total RNA (5-25 µg) from the heart, brain, lung, thymus and spleen of male mice, and ovary, endometrium, myometrium, cervix and vagina of female mice pooled from day 7.5, 10.5 and 18.5 of pregnancy, were run on standard MOPS/formaldehyde gels. RNA was then transferred to optimized Hybond-NX membranes and probed for M3 relaxin mRNA with a $^{32}$P-labeled probe that corresponded to the 319-bp PCR product, generated by specific primers to M3 relaxin (see above). This product was labeled with [α-$^{32}$P]dCTP using the specific reverse primer (above) and T7 polymerase as previously described (31). The membrane was hybridized at 65° C. overnight in 0.25M NaH$_2$PO$_4$, pH 7.2, 1 mM EDTA, 20% SDS, followed by three washes for 5 min in 2×SSC, 0.1% SDS at room temperature, and finally a 30 min wash at 65° C. in 0.1×SSC, 0.1% SDS. Membranes were first exposed to a phosphoimager plate for 48 h at room temperature before being analysed in a FujiX 2000 Phosphoimager (Fuji Photo Company, Japan), and then exposed to BioMAX MS film (Integrated Sciences, Melbourne, Australia) together with a Hyperscreen (Amersham Pharmacia, Sydney, Australia) at −80° C. In separate experiments, total RNA (200 µg) from the brain, spleen, liver and testes was purified to poly-A RNA using an niNA purification kit (Amersham Pharmacia), and Northern blotting performed as described above. A human multiple tissue expression array (CLONTECH laboratories, Palo Alto, Calif.) was hybridized with a $^{32}$P-labeled H3 relaxin specific probe according to the manufacturers recommendations. The 374-bp fragment of the H3 relaxin sequence isolated from genomic DNA was labeled with [α-$^{32}$P]dCTP using the H3 relaxin specific reverse primer (described above), and T7 polymerase (Bathgate et al (1999) *Biol. Reprod.* 61, 1090-1098). The membrane was exposed to a phosphoimager plate and BioMAX film as described above.

In Situ Hybridization Histochemistry—

Coronal sections (14 µm) were cut on a cryostat at −16° C. and mounted on silane-coated slides. Sections were delipidated in chloroform for 10 min, rinsed and stored in 100% ethanol at 4° C. Three oligonucleotides (39 mers) [5' GGTG-GTCTGTATTG GCTTCTCCATCAGCGAAGAAGTCCC 3' (SEQ ID NO:58)]; [5' AATTTGGCTCTTGCTACAGC-CCCACTC GCACGAACTGCT 3' (SEQ ID NO:26)] and [5' TAAGGAGACAGTGGACCCCTTGGTGCCTCGCCTGT AGGA 3' (SEQ ID NO:27)], of the M3 relaxin mRNA sequence, and three oligonucleotides to [5' GCACATC-CGAATGAATCCGTCCATCCACTCCTCCGAGAC 3' (SEQ ID NO:28)], [5' CAAGCAGAGCT GGCTCCTCCTG-GCTCAAAGCCAATCTTC 3' (SEQ ID NO:29)] and [5' GTTGTAGCTCTGGGAGCGAGGC CTGAGCCTCAGA-CAGTA 3' (SEQ ID NO:30)] of the previously known M1 relaxin sequence (Evans et al (1993) *J. Mol. Endocrinol.* 10, 15-23) were prepared commercially (Geneworks Pty Ltd). Probes were labeled with [α-$^{35}$S]dATP (1200 Ci/mmol; NEN, AMRAD-Biotech, Melbourne, Australia) to a specific activity of 1×10$^9$ d.p.m./µg using terminal deoxynucleotidyl transferase (Roche Diagnostics; Wisden et al (1994) In *In Situ Hybridization Protocols for the Brain* (Wisden, W. and Morris, B. J. eds), pp 9-34, Academic Press, London). Screening of the sequences used against gene sequence databases (Celera, EMBL and Genbank; NCBI/NIH Blast Service) revealed homology only with the appropriate M1 and M3 relaxin mRNAs.

Sections were incubated overnight at 42° C. with multiple $^{35}$S-labeled probes (30 fmol each probe/slide) in hybridization buffer containing 50% formamide, 4×SSC, 10% dextran sulphate and 0.2 M dithiothreitol. Slides were washed in 1×SSC at 55° C. for 1 h, rinsed in 0.1×SSC, then dehydrated before being apposed to Kodak BioMAX MR for 10 d.

The authenticity of the hybridization was confirmed by the demonstration that the signal could be successfully blocked in all areas by the addition of a 100-fold excess of unlabeled probes to the hybridization buffer, except those that corresponded to non-specific or background hybridization (data not shown). In addition, three oligonucleotide probes were used that were complementary to different, non-overlapping regions of the M3 relaxin gene sequence.

Human Relaxin (H3) Studies:

Solid Phase Synthesis—

A putative peptide sequence encoded by the H3 gene was assembled by solid phase synthesis procedures based on the predicted signal peptide and proteolytic enzyme cleavage sites between the signal peptide and the B-chain, and the B/C and C/A chain junctions of the H3 relaxin prohormone (see Results for details). For ease of synthesis we chose to prepare the A- and B-peptides as their carboxyl-terminal amide derivatives. Selectively S-protected A- and B-chains were synthesized on a 0.1 mmol scale by the continuous flow Fmoc solid-phase method as previously described Dawson et al (1999) *J. Pept Res.* 53, 542-547. Selective S-protection was afforded for the following cysteine residues: trityl (Trt) for A$^{10,15}$ and B$^{22}$, tert-butyl for A$^{24}$, and acetamidomethyl (Acm) for A$^{11}$ and B$^{10}$ (see FIG. 2A for numbering of amino acid residues).

On completion of the syntheses, the S-protected A- and B-chains were cleaved from the solid supports and simultaneously sidechain deprotected by treatment with TFA in the presence of scavengers. Selective disulfide bond formation was achieved essentially as described for the synthesis of bombyxin Maruyama et al (1992) *J. Prot. Chem.* 11, 1-12.

Peptide Characterization—

Peptides were quantitated by duplicate amino acid analysis of 24 h acid hydrolyzates on a GBC automatic analyser (Melbourne, Australia). MALDITOF mass spectrometry (MS) was performed in the linear mode at 19.5 kv on a Bruker Biflex instrument (Bremen, Germany) equipped with delayed ion extraction.

Other Relaxin and Insulin Peptides—

Human INSL3 was synthesized using the same methodology used for ovine INSL3 (Dawson et al (1999) *J. Pept. Res.* 53, 542-547), and was characterized by MS and amino acid analysis as outlined above. H1 relaxin was synthesized previously (Wade et al (1996) *Biomed. Pept. Prot. Nucl. Acids* 2, 27-32), recombinant H2 relaxin was a gift from the Connetics Corporation (Palo Alto, Calif.) and bovine insulin was purchased from Roche Diagnostics (Sydney, Australia).

THP-1 Cell Bioassay—

The ability of H3 relaxin to induce cAMP production in the human monocytic cell line (THP-1) was compared to H1 and H2 relaxin following the procedure of Parsell and colleagues (Parsell et al (1996) *J. Biol. Chem.* 271, 27936-27941), with the following modifications; THP-1 cells which had been viability tested using Trypan Blue were resuspended in media, and transferred to a 96 well plate at a density of 60,000 cells/well. Peptides (H1, H2, H3 relaxin, human INSL3 and bovine insulin) were added to the wells together with 1 µM forskolin and 50 µM isobutylmethylxanthine (IBMX) in RPMI media, and incubated at 37° C. for 30 min. The plate was then briefly centrifuged, the media removed and the cells resuspended in lysis buffer. cAMP levels were measured in the lysates using the cAMP Biotrak EIA system (Amersham International, Aylesbury, UK). The results are expressed as the maximum relaxin response (%) in comparison to the maximum stimulation of cAMP achieved with H2 relaxin. Data represent the mean±SEM of three experiments performed in quadruplicate, and are plotted using PRISM (Graphpad Inc., San Diego, Calif.).

THP-1 Cell Binding Assay—

THP-1 cells were spun down and resuspended in binding buffer (20 mM HEPES, 50 mM NaCl, 1.5 mM $CaCl_2$, 1% BSA, 0.1 mg/ml lysine, 0.01% $NaN_4$, pH 7.5) (Parsell et al (1996) *J. Biol. Chem.* 271, 27936-27941) to give $2\times10^6$ cells/well in a 96-well plate. The cells were incubated in binding buffer with $^{33}$P-labeled H2 (B33) relaxin (100 pM: labeled as previously described (Tan et al (1999) *Br. J. Pharmacol.* 127, 91-98) at 25° C. for 90 min in the absence or presence of increasing concentrations of unlabeled H1, H2 and H3 relaxin (100 µM to 30 nM). Non-specific binding was defined with H2 relaxin (1 µM). Cells were harvested using a Packard 96-well plate cell harvester and Whatman GF/C glass fibre filters treated with 0.5% polyethylenimine. The filters were washed three times with modified binding buffer (20 mM HEPES, 50 mM NaCl, 1.5 mM $CaCl_2$), dried in a 37° C. oven, and the radioactivity counted by liquid scintillation spectrometry (TopCount™, Canberra Packard, Australia).

Antibody Crossreactivity—

The ability of well characterized human relaxin antibodies to recognize H3 relaxin was tested in comparison to H1 and H2 relaxins by radioimmunoassay. Briefly, goat anti-H2 relaxin (Lucas et al (1989) *J. Endocrinol.* 120, 449-57) was coated onto 96 well ELISA plates (Disposable Products, Adelaide, Australia) at a dilution of 1:1000 with 0.05M sodium carbonate buffer at 4° C. overnight. After washing twice with PBS-T (phosphate buffered saline; 0.05% Tween 20, pH 7.4) dilutions of human relaxin peptides dissolved in 50 µl of assay buffer (1% BSA in PBS-T) were added together with 50,000 cpm $^{125}$I-labeled relaxin, in 50 µl of assay buffer. H2 relaxin was $^{125}$I-labeled and purified by HPLC (Palejwala et al (1998) *Endocrinology* 139, 1208-1212). After an overnight incubation at 4° C. the plates were washed twice with PBS-T. The antibody-bound-$^{125}$I-labeled H2 relaxin was collected by the addition of 1M NaOH and decanted into tubes for counting on a Packard 5010 gamma counter (Canberra Packard). Experiments were performed at least twice and similar results obtained. Data was plotted as the mean±SEM from one representative experiment performed in triplicate and plotted using PRISM.

Mouse Relaxin (M3) Studies:

Animals—

All male and female mice used in these studies were age-matched and had the same background (C57BLK6J). Animals were housed in a controlled environment and maintained on a 14 h light, 10 h dark schedule with access to rodent lab chow (Barastock Stockfeeds, Melbourne, Australia) and water. Female mice (3.5 months old) were mated and pregnancy timed from the identification of the vaginal plug. At day 7.5, 10.5 and 18.5 of pregnancy, mice were sacrificed for tissue collection. Tissues were also collected from non-pregnant female and male mice (4 months old). These experiments were approved by the Howard Florey Institute's Animal Experimental Ethics Committee, which adheres to the Australian Code of Practice for the care and use of laboratory animals for scientific purposes.

Tissue Collection—

Animals were killed with an overdose of Isofluorane (Abbott Australasia Pty Ltd, Sydney, Australia). The brain, heart, thymus, spleen, lung, liver, kidneys, skin and gut were collected along with the reproductive organs from female (ovary, endometrium, myometrium, cervix, vagina; n=2 for each pregnancy stage) and male (testes, epididymis, prostate; n=3) mice. From additional animals, male brains (n=3) were dissected into specific regions including the hypothalamus, cortex, hippocampus, thalamus, medulla and cerebellum, and immediately placed in liquid nitrogen and stored at −80° C. until used for RNA preparation. Female brains (n=3) were collected and immediately frozen over dry ice for in situ hybridization histochemistry (Burazin et al (2001) *J. Neuroendocrinol.* 13, 358-370). Human CL from women in early pregnancy undergoing surgery for ectopic pregnancies were utilized with the approval of the Howard Florey Institute Human Ethics Committee and the written consent of the patients.

EXAMPLE 2

Human H3 Relaxin Genes in the Human and Mouse

Both H3 relaxin sequences in the human and mouse contain features representative of functional genes (FIG. 1A human; 1B mouse). Each contain a putative TATA box for initiation of transcription 65, and 59 bp, upstream of putative ATG start codons for human and mouse, respectively. A polyadenylation signal is present in the 3' untranslated region of both genes, in a position 582 and 448 bp downstream from an inframe TAG stop codon for the human, and mouse genes respectively. A single intron interrupts the coding region in an identical position in the sequence of both genes, corresponding to a similar position to that of other relaxin and insulin family members (Hudson et al (1983) *Nature* 301, 628-631; Evans et al (1993) *J. Mol. Endocrinol.* 10, 15-23; Ivell, R (1997) *Rev. Reprod.* 2, 133-138). The H3 relaxin gene is localized on chromosome 19 at 19p 13.3, whereas the mouse gene is located on chromosome 8 at 8C2. The derived coding regions of the H3 and M3 relaxin genes were 142, and 141, amino acids, respectively.

The cysteine residues necessary for disulphide bond formation are retained in the correct positions, together with conserved glycine residues necessary for flexibility around the cysteine linkages (Büillesbach et al (2000) *Int. J. Pept. Prot. Res.* 46, 238-243). Most importantly, the residues demonstrated to be essential for relaxin receptor binding in the core of the B-chain (R—X—X—X—R—X—X—I) (Büllesbach et al (2000) *J. Biol. Chem.* 275, 35276-35280), have been retained in both the human and mouse sequences. Therefore, although the human sequence most closely resembles the hINSL5 peptide sequence on direct amino acid homology, the presence of this binding motif indicates that the peptide is more like a relaxin peptide. Interestingly, the M3 relaxin A-chain conforms to the cysteine pattern of family members, whereas the previously characterized M1 relaxin sequence contains an extra tyrosine residue before the final cysteine residue (FIG. 2A).

The H3 (human H3) and M3 (mouse "3" relaxin) sequences share greater than 70% homology in the coding region at the nucleotide level. However, the homology is most striking in the derived amino acid sequence. Both derived pro-hormone sequences contain a typical signal sequence after the ATG start codon which is likely to be cleaved at an identical position between alanine and arginine in both the human and mouse peptides (Nielsen et al (1997) *Prot. Engineer.* 10, 1-6). The arginine-arginine pair of basic amino acids at the B/C junction found with other members of the relaxin family strongly suggests cleavage between tryptophan and arginine. Similarly, cleavage at the C/A junction is most likely to occur between the arginine and aspartic acid as indicated in FIGS. 1A and 1B, as this corresponds to a weak furin (pro-protein convertase) cleavage site (Nakayama, K. (1997) *Biochem. J.* 327, 625-635. Therefore, it is believed that both H3 and M3 relaxins comprise a B-chain of 27 amino acids, a C-peptide of 66 amino acids and an A-chain of 24 amino acids.

A comparison of the A- and B-chain sequences of H3 and M3 relaxin with H1, H2 and M1 relaxin is outlined in FIG. 2A. There are only two amino acid differences in both the A- and B-chains between the M3 and H3 sequences, of which three of these changes are conserved. In contrast, the homology between M1 and H2 relaxin is only 42% and 45% in the A-, and B-, chains respectively. Furthermore, other than the key core elements in the B-chain and the key structural elements in the A-chain, there is very little homology between H2 and H3 relaxin, and between M1 and M3 relaxin. Interestingly, H3 and M3 relaxin show high homology of the C-peptide domain (73%), compared with less than 20% homology in this region of other insulin/relaxin family members. The C-peptide lengths of H3 and M3 relaxin are 65, and 66 amino acids, respectively, and are much shorter than that of other relaxins (102 amino acids for H1 and H2 and 99 amino acids for M1 relaxin). The C-peptide chain length and sequence homology is most similar to INSL5 (24%).

The full length amino acid sequences of the two genes were aligned to other members of the insulin/relaxin family and a phylogenetic tree generated (FIG. 2B). Additionally, the H3 and M3 relaxin sequences are grouped under a separate branch, indicating that the evolution of these particular relaxins diverged from other relaxins early in evolution. This was also the case for INSL5 within this analysis which interestingly shares closest primary structural similarity to H3 relaxin.

EXAMPLE 3

Peptide Synthesis

H3 relaxin was prepared by solid phase synthesis in low overall yield (0.7%). MALDITOF MS showed a single product with an MH$^+$ of 5,494.7 (theoretical value: 5,497.5). Amino acid analysis also confirmed its correct composition. Chemical Synthesis of Human Relaxin H3 [hR]x-3 A (1-24) Amide-B (1-27) Amide Selectively S-protected A- and B-chains representing the amino acid sequence of the separate H3 relaxin peptide chains, were synthesized by the continuous flow 9-fluorenyl methoxycarbonyl (Fmoc) solid-phase method using the general procedures described in Atherton, E and Sheppard, RC. (*Solid Phase Peptide Synthesis*. IRL Press at Oxford University Press, Oxford, United Kingdom, 1989). Both peptides were prepared on a 0.1 mmol scale as peptide-carboxyl terminal amides using Fmoc peptide amide linker polyethylene glycol polystyrene (Fmoc-PAL-PEG-PS) supports (Applied Biosystems). For the A-chain assembly, four-fold excesses of Fmoc-amino acids (Auspep, Melbourne, Australia) were activated by 1,3-diisopropylcarbodiimide (DIC) and 1-hydroxybenzotriazole (HOBt) in dimethylformamide (DMF), whereas during the B-chain synthesis each residue was activated by 2-(1H-benzotrazole-1-yl)-1,1,3,3-tetramethyluronium hexafluorophosphate (HBTU) and diisopropylethylamine (DIEA) in DMF. $N^\alpha$-Fmoc deprotection for both chain assemblies was with 20% piperidine in DMF. Couplings were generally of 30 minutes duration, with the exception of double couplings and extended times for A-chain residues Ser$^{7,8,21}$ and all cysteines, and double couplings of B-chain residues Arg$^{1,12,16}$, Ala$^{2,3,17}$ and Cys$^{10}$. Side chain protection was afforded by tert-butyl esters and ethers for Asp, Glu, Thr and Ser, butoxycarbonyl (Boc) for Lys and Trp, 2,2,4,6,7-pentamethyldihydrobenzofurane-5-sulfonyl (Pbf) for Arg and the amide bond protection $N^\alpha$-(2-Fmoc-oxy-4-methoxybenzyl) [FmocHmb] for B-chain Gly$^{11}$. Selective S-protection was afforded for the following cysteine residues: trityl (Trt) for Cys$^{10,15}$ in the A-chain and Cys$^{22}$ in the B-chain, tert-butyl (tBu) for Cys$^{24}$ in the A-chain, and acetamidomethyl (Acm) for A-chain Cys$^{11}$ and B-chain Cys$^{10}$.

(i) Synthesis of Human Relaxin H3, A-Chain [Cys$^{11}$(Acm), Cys$^{24}$(tBu)](1-24) Amide [1]

On completion of the synthesis, the protected A-chain resin was treated at room temperature for 2.5 hours with 95% trifluoroacetic acid (TFA)/2.5% ethanedithiol (EDT)/2.5% H$_2$O plus 4 drops triethylsilane, to aid the quenching of thiols. TFA was removed to a minimum volume under a stream of nitrogen and precipitated twice from chilled diethyl ether. The precipitate was then dissolved in 0.1% aq. TFA and lyophilized. The crude S-reduced [thiol-Cys$^{10,15}$, Cys$^{11}$ (Acm), Cys$^{24}$(t-Bu)] A-chain was directly subjected to air oxidation in 0.1M Gly-NaOH, pH 8.3, for 4 hours at room temperature. Analytical reverse-phase high performance liquid chromatography (RP-HPLC) monitoring confirmed the completeness of the intramolecular disulfide bond formation, after which several drops of neat TFA were added and the crude oxidized material directly lyophilized.

(ii) Synthesis of Human Relaxin H3, B-Chain [Cys$^{10}$(Acm)] (1-27) Amide [2]

On completion of the synthesis, the protected B-chain resin was treated at room temperature for 2.5 hours with 82.5%

TFA/5% phenol/5% H$_2$O/5% thioanisole/2.5% ethanedithiol plus 4 drops of triethylsilane, to aid the quenching of thiols. TFA was removed to a minimum volume under a stream of nitrogen and precipitated twice from chilled diethyl ether. The precipitate was then dissolved in 0.1% aq. TFA and lyophilized. The crude B-chain was then purified by RP-HPLC as described below.

(iii) Synthesis of Human Relaxin H3, A-Chain [Cys$^{11}$(Acm), Cys$^{24}$(Pyr)](1-24) Amide [3]

25 mg of peptide 1 (9.65 μmol) and 35 mg (158.86 μmol) 2,2'-dipyridyl disulfide (DPDS) were dissolved together in 4.5 ml TFA and 0.5 ml thioanisole and the resulting solution then chilled. To this was added 5 ml trifluoromethanesulfonic acid (TFMSA)/TFA (1:5 v/v) and the whole mixture allowed to stir at <0° C. for 30 mins. The [Cys$^{11}$(Acm), Cys$^{24}$(Pyr)] A-chain amide peptide was precipitated from cold ether and the pellet obtained on centrifugation then suspended in 6M guanidine hydrochloride (GdHCl), pH 8.0, and purified by RP-HPLC. (Yield peptide 3: 4%). (Alternative to RP-HPLC purification, peptide 3 was desalted on a Sephadex G-25 gel filtration column in 20% aq acetic acid).

(iv) Synthesis of Human Relaxin H3. A[Cys$^{11}$(Acm)](1-24) Amide-B[Cys$^{10}$(Acm)](1-27) Amide [4]

Purified A-chain peptide 3 (1.0 mg, 0.38 μmol) and purified B-chain peptide 2 (1.2 mg, 0.38 μmol) were dissolved separately in 1.0 ml and 0.5 ml 0.1M NH$_4$HCO$_3$ respectively. The B-chain solution was then slowly added to A-chain and the reaction mixture was stirred vigorously at room temperature for 30 min. The solution was acidified with 0.5 ml glacial acetic acid and then subjected to RP-HPLC, as detailed below, to isolate the bis-disulfide bonded chain combined product. (Alternative to RP-HPLC purification, the resulting A/B product, peptide 4, was desalted on a Sephadex G-25 gel filtration column in 20% aq acetic acid).

(An alternative method for chain combination which improves B-chain solubility, is as follows: peptide 3 and purified [Cys$^{10}$(Acm)] B-chain were dissolved separately, at a concentration of 1.0 ml/mg, in 8M GdHCl, pH 4.5 buffer. The B-chain solution was then slowly added to A-chain and the reaction mixture was stirred vigorously at 37° C. for 24 hours).

(v) Synthesis of Human Relaxin H3 [hR]x-3A (1-24) Amide-B (1-27) Amide

All of the purified 4 peptide was used to form the third and final disulfide bond (assuming 100% recovery, estimated at 0.39 μmol). The peptide was dissolved in a solution of 80 nm. HCl and acetic acid. 20 mM iodine in 95% aqueous acetic acid was then added dropwise (25 equivs of iodine per Acm group). The reaction was performed for 1 hour in the dark at room temperature after which excess oxidant was quenched with 20 nM aqueous ascorbic acid. Purification of the relaxin was by RP-HPLC, with a final yield, relative to peptide 3 starting material, of 0.74%.

Purification

The separate crude chains and intermediate peptides were purified by RP-HPLC, using a Waters 600 multisolvent delivery system connected to a model 996 photodiode array detector. A 10×250 mm Vydac 218 TP column packed with C$_4$ silica gel (330 A pore size, 10 μm particle size) was used. The peptides were eluted with a solvent system of (A) 0.1% aq. TFA (v/v) and (B) 0.1% TFA in acetonitrile (v/v) in a linear gradient mode (25-50% B over 30 minutes). The target fractions were collected and identified by matrix-assisted laser desorption ionization mass spectrometry (MALDI-TOF MS) and lyophilized.

Peptide Characterisation

Peptide quantitation was by duplicate amino acid analysis of 24 hr acid hydrolyzates on a GBC automatic analyser (Melbourne, Aust). MALDITOF MS was performed in the linear mode at 19.5 kv on a Bruker Biflex instrument (Bremen, Germany) equipped with delayed ion extraction.

EXAMPLE 4

Relaxin Biological Activity

Demonstration of Relaxin Activity of Synthetic H3 Relaxin—

Synthetic H3 relaxin C-terminal amide derivatives were tested for relaxin activity in a relaxin receptor expressing cell line, THP-1 (Parsell et al (1996) *J. Biol. Chem.* 271, 27936-27941). H2 relaxin produces a dose dependent increase in cAMP production from these cells (FIG. 3A). Synthetic H3 relaxin also stimulated a dose dependent increase in cAMP (pEC$_{50}$=8.68±0.08 [2.11 nM]; n=3), albeit with slightly lower activity than H1 (pEC$_{50}$=9.10±0.05 [0.794 nM]; n=3) and H2 (pEC$_{50}$=9.67±0.11 [0.214 nM]; n=3) relaxin. The specificity of this response was demonstrated by the inability of bovine insulin (bINSL), or human insulin 3 (hINSL3), to stimulate cAMP responses at doses up to 1 μM.

Synthetic H3 relaxin was also tested for its ability to compete for $^{33}$P-labeled H2 relaxin binding to relaxin binding sites in THP-1 cells (FIG. 3B), with an affinity (pK$_i$=7.5±0.16; n=3) lower than that of H2 (pK$_i$=8.74±0.11; n=11) and H1 (pK$_i$=8.9+0.11; n=7) relaxin. Nevertheless, these data provide definitive evidence that the synthetic H3 relaxin peptide binds to, and elicits a second messenger response by stimulating human relaxin receptors.

Ability of a Well Characterized H2 Relaxin Antibody to Recognize H3 Relaxin—

The ability of a well characterized anti-H2 relaxin antibody to recognize H1 and H3 relaxin was tested by radioimmunoassay. As shown in FIG. 4, H2 relaxin was able to displace $^{125}$I-labeled H2 relaxin binding to the anti-H2 relaxin antibody with high specificity. In contrast, H1 and H3 relaxin showed poor cross reactivity with the antisera as determined by their poor ability to displace $^{125}$I-labeled H2 relaxin binding. Furthermore, the non-parallellism of the displacement curves indicates that not all the antibody epitopes are recognized by the two peptides.

EXAMPLE 5

H3 Relaxin Expression

Relaxin Gene Expression in the in the Mouse—

The expression of M3 relaxin mRNA was compared to M1 relaxin mRNA expression using southern blotting of RT-PCR products. Although this technique is only semi-quantitative, it enabled us to determine the potential sites of expression of M3 relaxin compared to M1 relaxin. The results of a representative experiment and duplicate experiments gave identical results. M3 relaxin mRNA was expressed in a number of tissues in C57BLK6J mice where M1 relaxin was found, but the pattern of expression, between the two mouse relaxins was different. In male non-reproductive tissues, highest levels of M1 relaxin expression were seen in the brain, moderate levels in the thymus, heart and kidney, lower levels in the lung, spleen and skin, with no expression seen in the gut. Interestingly, M3 relaxin expression was detected at highest levels in brain, however, it was expressed at moderate levels in the thymus, lung and spleen, only at very low levels in the heart and liver, and not at all in the kidney, skin and gut. Female mice showed an almost identical pattern of expression for both genes in these tissues. In male reproductive tissues M3 relaxin mRNA was significantly expressed only in the testis whereas, M1 relaxin mRNA was detected in the testis, epididymis and prostate. Both relaxins were also detected in female reproductive organs in the mammary gland, ovaries of non-pregnant, pregnant and lactating mice, and the endometrium and myometrium of pregnant mice. Significant expression of M3 relaxin mRNA was observed in all ovarian stages, while M1 relaxin expression was higher in ovaries of late gestation compared to ovaries from non-pregnant and lactating mice. High levels of M3 relaxin mRNA were detected in the brain and further analysis of this tissue revealed that both relaxins were expressed in several distinct regions. While M1 relaxin mRNA was consistently expressed in the hypothalamus, hippocampus, cortex, thalamus, pons/medulla and cerebellum, M3 relaxin mRNA was found to be highly expressed in the thalamus and pons/medulla, thus suggesting, that the two relaxins may play distinct roles in the mouse.

Northern Analysis—

Tissues in which M3 relaxin M1 RNA was positively identified by RT-PCR and Southern blot analysis, were further examined by Northern blotting. Total RNA (5-25 µg) from the heart, brain, lung, thymus, spleen, ovary, endometrium, myometrium, cervix and vagina were initially probed with a $^{32}$P-labeled M3 relaxin specific probe, but no specific hybridizing bands were found in any tissue. Poly-A RNA from the brain (15 µg), spleen (5 µg), liver (5 µg) and testis (25 µg) were then analyzed and a specific ~1.2-kb hybridizing band was identified in the brain, consistent with M3 relaxin expression detected by RT-PCR and Southern blot analysis. The obtained transcript size was consistent with the predicted size based on the M3 relaxin transcript sequence (~1 kb) plus a poly-A tail (~200-bp).

Expression of H3 Relaxin in Human Tissues—

A Clonetech Multi Tissue Expression Array was used to examine sites of expression of H3 relaxin in human tissues. The array contained normalized poly-A RNA (50-750 ng) from 76 different human tissues including 8 different control RNAs and DNAs, spotted onto a nylon membrane. The array was probed with a $^{32}$P-labeled 374-bp H3 relaxin specific gene fragment from the 3' end of the H3 relaxin transcript, generated from genomic DNA. This DNA fragment was sequenced on both strands. Very weak hybridizing signals were observed in spleen, thymus, peripheral blood leukocytes, lymph node and testis however, these signals were barely discernable above background and hence, the data is not shown. RT-PCR was also performed on human CL from early pregnancy using two different primer combinations based on the H3 relaxin sequence. No specific bands were observed in any PCR reaction even after changing the PCR conditions, whereas transcripts for H2 relaxin and GAPDH were easily amplified (data not shown), confirming the integrity of the cDNA.

Distribution of Relaxin mRNA in the Mouse Brain—

Given the high levels of M3 relaxin mRNA expression detected by RT-PCR and Northern blotting in the brain, its distribution was further examined using in situ hybridization histochemistry (Burazin et al (2001) *J. Neuroendocrinol.* 13, 358-370. Multiple specific $^{35}$S-labeled oligonucleotide probes were utilized to determine the cellular distribution of M3 relaxin mRNA throughout the rostro-caudal extent of the female C57BLK6J mouse brain. M3 relaxin mRNA was not widely detected throughout brain nuclei, but was most strongly detected in the pons/medulla (FIG. 7). The strongest level of M3 relaxin mRNA was present in the pars ventromedialis of the dorsal tegmental nucleus. In addition, M3 relaxin mRNA was also detected, albeit at far lower levels, in the hippocampus and olfactory regions. Brain regions containing low levels of mRNA encoding M3 relaxin may not have been detected in the current study due to sensitivity limitations associated with in situ hybridization histochemistry. The distribution of M3 relaxin mRNA in the brain differs from that of M1 relaxin mRNA, as no M1 relaxin mRNA was detected in the pars ventromedialis of the dorsal tegmental nucleus (data not shown).

EXAMPLE 6

Prorelaxin H3 cDNA sequences from human, mouse and rat are expressed in both prokaryotic and eukaryotic cell systems using appropriate expression transfer vectors.

These systems include appropriate mammalian host cells, other higher eukaryotic cells including insect cells, plant cells and avian cells as well as bacterial and yeast expression systems. Additionally, fusion protein products of these three sequences are produced by linking a portion of a prokaryotic or eukaryotic protein characteristic of the host cell. The fusion products facilitate the purification of the protein product such that the fusion product may be subsequently removed. All transfer vectors may also be modified by codon substitutions/deletions/additions with the modifications giving rise to shortened C peptide prorelaxins with B/C and C/A junction modifications to facilitate the removal of the modified C peptide sequence.

Relaxin synthesis using shortened C peptide substitutions and B/C and C/A junction modifications are described in U.S. Pat. No. 5,759,807, and such methods may be used for the production of H3 relaxin.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The reference to any prior art in this specification is not, and should not be taken as an acknowledgment or any form of suggestion that that prior-art forms part of the common general knowledge in Australia.

The claims defining the invention are as follows:

1. A method for treating anxiety comprising administering to a subject suffering from anxiety a therapeutically effective amount of human H3 relaxin, wherein said human H3 relaxin comprises an A chain and a B chain; wherein said A chain is at least 95 percent identical to the amino acid sequence of SEQ ID NO:45 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

2. The method of claim 1, wherein said human H3 relaxin further comprises carriers, diluents or excipients, and mixtures thereof.

3. The method according to claim 1, wherein said H3 relaxin comprises a C chain.

4. The method according to claim 3, wherein said C chain comprises the amino acid sequence of SEQ ID NO:3.

5. The method according to claim 3, wherein said B chain comprises the amino acid sequence of SEQ ID NO:2 and wherein said C chain comprises the amino acid sequence of SEQ ID NO:3.

6. The method according to claim 3, wherein the carboxy terminus of the amino acid sequence of SEQ ID NO:2 is an amide derivative.

7. The method according to claim 1, wherein said H3 relaxin comprises a signal sequence.

8. The method according to claim 7, wherein said signal sequence comprises the amino acid sequence of SEQ ID NO:1.

9. The method according to claim 1, wherein said H3 relaxin further comprises a signal sequence and a C chain.

10. The method according to claim 9, wherein said signal sequence comprises the amino acid sequence of SEQ ID NO:1, said B chain comprises the amino acid sequence of SEQ ID NO:2 and wherein said C chain comprises the amino acid sequence of SEQ ID NO:3.

11. The method according to claim 1, wherein said B chain comprises the amino acid sequence of SEQ ID NO:2.

12. The method according to claim 1, wherein said B chain comprises the amino acid sequence of SEQ ID NO:37.

13. The method according to claim 1, wherein said B chain comprises the amino acid sequence of SEQ ID NO:2.

14. The method according to claim 1, wherein said B chain comprises an amino acid sequence having at least 95 percent identity to the amino acid sequence of SEQ ID NO:37.

15. The method according to claim 1, wherein said human H3 relaxin comprises a B chain having at least 85 percent identity to the amino acid sequence of SEQ ID NO:2.

16. The method according to claim 1, wherein the carboxy terminus of the amino acid sequence of SEQ ID NO:37 is an amide derivative.

17. A method for treating anxiety comprising administering to a subject suffering from anxiety a therapeutically effective amount of human H3 relaxin, wherein said human H3 relaxin comprises an A chain and a B chain; wherein said A chain comprises the amino acid sequence of SEQ ID NO:45 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

18. The method according to claim 17, wherein the carboxy terminus of the amino acid sequence is an amide derivative.

19. A method for treating anxiety comprising administering to a subject suffering from anxiety a therapeutically effective amount of human H3 relaxin, wherein said human H3 relaxin comprises an A chain and a B chain; wherein said A chain consists of the amino acid sequence of SEQ ID NO:45 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

20. A method for treating anxiety comprising administering to a subject suffering from anxiety a therapeutically effective amount of human H3 relaxin, wherein said human H3 relaxin comprises an A chain and a B chain; wherein said A chain is at least 85 percent identical to the amino acid sequence of SEQ ID NO:4 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

21. A method for treating anxiety comprising administering to a subject suffering from anxiety a therapeutically effective amount of human H3 relaxin, wherein said human H3 relaxin comprises an A chain and a B chain; wherein said A chain comprises the amino acid sequence of SEQ ID NO:4 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

22. The method of claim 21, wherein said human H3 relaxin further comprises carriers, diluents or excipients, and mixtures thereof.

23. The method according to claim 21, wherein said H3 relaxin comprises a C chain.

24. The method according to claim 21, wherein said H3 relaxin comprises a signal sequence.

25. The method according to claim 21, wherein said H3 relaxin comprises a signal sequence and a C chain.

26. The method according to claim 25, wherein said signal sequence comprises the amino acid sequence of SEQ ID NO:1, said B chain comprises the amino acid sequence of SEQ ID NO:2 and wherein said C chain comprises the amino acid sequence of SEQ ID NO:3.

27. The method according to claim 21, wherein said B chain comprises the amino acid sequence of SEQ ID NO:2.

28. The method according to claim 21, wherein said C chain comprises the amino acid sequence of SEQ ID NO:3.

29. The method according to claim 21, wherein said signal sequence comprises the amino acid sequence of SEQ ID NO:1.

30. The method according to claim 21, wherein said B chain comprises the amino acid sequence of SEQ ID NO:2 and wherein said C chain comprises the amino acid sequence of SEQ ID NO:3.

31. The method according to claim 21, wherein the carboxy terminus of the amino acid sequence is an amide derivative.

32. A method for treating anxiety comprising administering to a subject suffering from anxiety a therapeutically effective amount of human H3 relaxin, wherein said human H3 relaxin comprises an A chain and a B chain; wherein said A chain consists of the amino acid sequence of SEQ ID NO:4 and wherein said B chain comprises the amino acid sequence of SEQ ID NO: 2, the amino acid sequence having at least 85 percent identity to SEQ ID NO: 2, the amino acid sequence of SEQ ID NO: 37, or the amino acid sequence having at least 95 percent identity to SEQ ID NO: 37.

* * * * *

SEQUENCE LISTING

```
<160> NUMBER OF SEQ ID NOS: 58

<210> SEQ ID NO 1
<211> LENGTH: 25
<212> TYPE: PRT
<213> ORGANISM: Homo sapiens

<400> SEQUENCE: 1

Met Ala Arg Tyr Met Leu Leu Leu Leu Ala Val Trp Val Leu Thr
1               5                   10                  15

Gly Glu Leu Trp Pro Gly Ala Glu Ala
            20                  25
```

```
<210> SEQ ID NO 2
<211> LENGTH: 27
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ala or Pro
<220> FEATURE:
<221> NAME/KEY: MISC_FEATURE
<222> LOCATION: (8)..(8)
<223> OTHER INFORMATION: Xaa is Arg or Lys

<400> SEQUENCE: 2

Arg Xaa Ala Pro Tyr Gly Val Xaa Leu Cys Gly Arg Glu Phe Ile Arg
 1               5                  10                  15

Ala Val Ile Phe Thr Cys Gly Gly Ser Arg Trp
            20                  25

<210> SEQ ID NO 3
<211> LENGTH: 66
<212> TYPE: PRT
<213> ORGANISM: Homo sapiens

<400> SEQUENCE: 3

Arg Arg Ser Asp Ile Leu Ala His Glu Ala Met Gly Asp Thr Phe Pro
 1               5                  10                  15

Asp Ala Asp Ala Asp Glu Asp Ser Leu Ala Gly Glu Leu Asp Glu Ala
            20                  25                  30

Met Gly Ser Ser Glu Trp Leu Ala Leu Thr Lys Ser Pro Gln Ala Phe
        35                  40                  45

Trp Arg Gly Arg Pro Ser Trp Gln Gly Thr Pro Gly Val Leu Arg Gly
    50                  55                  60

Ser Arg
65

<210> SEQ ID NO 4
<211> LENGTH: 24
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Xaa is Lys or Glu
<220> FEATURE:
<221> NAME/KEY: MISC_FEATURE
<222> LOCATION: (19)..(19)
<223> OTHER INFORMATION: Xaa is Glu or Gln

<400> SEQUENCE: 4

Asp Val Leu Ala Gly Leu Ser Ser Ser Cys Cys Xaa Trp Gly Cys Ser
 1               5                  10                  15

Lys Ser Xaa Ile Ser Ser Leu Cys
            20

<210> SEQ ID NO 5
<211> LENGTH: 117
<212> TYPE: PRT
<213> ORGANISM: Homo sapiens

<400> SEQUENCE: 5

Arg Ala Ala Pro Tyr Gly Val Arg Leu Cys Gly Arg Glu Phe Ile Arg
 1               5                  10                  15

Ala Val Ile Phe Thr Cys Gly Gly Ser Arg Trp Arg Arg Ser Asp Ile
            20                  25                  30
```

| | | | | | | | | | | | | |
|---|---|---|---|---|---|---|---|---|---|---|---|---|
|Leu|Ala|His|Glu|Ala|Met|Gly|Asp|Thr|Phe|Pro|Asp|Ala|Asp|Ala|Asp|
| | |35| | | |40| | | |45| | | | | |

| | | | | | | | | | | | |
|---|---|---|---|---|---|---|---|---|---|---|---|
|Glu|Asp|Ser|Leu|Ala|Gly|Glu|Leu|Asp|Glu|Ala|Met|Gly|Ser|Ser|Glu|
| |50| | | | |55| | | | |60| | | | |

| | | | | | | | | | | | |
|---|---|---|---|---|---|---|---|---|---|---|---|
|Trp|Leu|Ala|Leu|Thr|Lys|Ser|Pro|Gln|Ala|Phe|Tyr|Arg|Gly|Arg|Pro|
|65| | | | |70| | | | |75| | | | |80|

| | | | | | | | | | | | |
|---|---|---|---|---|---|---|---|---|---|---|---|
|Ser|Trp|Gln|Gly|Thr|Pro|Gly|Val|Leu|Arg|Gly|Ser|Arg|Asp|Val|Leu|
| | | | |85| | | | |90| | | | |95| |

| | | | | | | | | | | | |
|---|---|---|---|---|---|---|---|---|---|---|---|
|Ala|Gly|Leu|Ser|Ser|Ser|Cys|Cys|Lys|Trp|Gly|Cys|Ser|Lys|Ser|Glu|
| | | |100| | | | |105| | | | |110| | |

| | | |
|---|---|---|---|
|Ile|Ser|Ser|Leu|Cys|
| | |115| | |

<210> SEQ ID NO 6
<211> LENGTH: 3449
<212> TYPE: DNA
<213> ORGANISM: Homo sapiens

<400> SEQUENCE: 6

```
tataaatggg gggccaagag gcagcagaga cactggccca ctctcacgtt caaagcgtct      60
ccgtccagca tggccaggta catgctgctg ctgctcctgg cggtatgggt gctgaccggg     120
gagctgtggc cgggagctga ggcccgggca gcgccttacg gggtcaggct ttgcggccga     180
gaattcatcc gagcagtcat cttcacctgc gggggctccc ggtggagacg atcagacatc     240
ctggcccacg aggctatggg tgaggctggg gagagagtgg atgtagaagg ggaacaggtg     300
gctggatggg tcccaggagc taaggacaga gataagagga ggttgctgga ggaggagggt     360
ccctgtcctg ccacattcag ccagggacac ctgcccagcc ttgaaacaag ggctcaggag     420
ttagcagagc tgcagagctg ggatggggtg ttgcaagcca tccatggggg ctggaagtct     480
gaggacaggt gggggcgggg agcgtgccat ttgcaaagac aacaccgaag tgttttccaa     540
ccctttccag caggtaatgt gaagggtgtg gtatacacat agctgggttt gtcacctaat     600
gcatgacctc tccccagcaa gttggttttt cttccgtctc tgagtgtctt tttttggag     660
atgtggtctc actccattgc ccaggcttga atgcagtggc ccaatcactg ctcattgcag     720
cctcgacctc ccaggctcaa gtgattctcc tgcctccgcc tccagagtag ttgagaccac     780
aggcacctga caccatgcct ggctagtttt aaatttttt tttgtagaaa caggggtctc      840
actatgttgc ctaggctggt ctcgaactcc tgggctcaag tgatcctccc acctcggcct     900
ccctaagtgc tgagattaga gtctctgagt gtctttatct tcaaatggga gacacagttc     960
ctgaatcttg caggattaag tggtatgatt aaatcaaaac agattagggc agagtctcag    1020
cagggcagcg gcacaatctg ggatccatca ggagagtcag agggaacaga agacctagct    1080
tcatgagggg cagggacctg gcaaatagat attcatgatg gtgagaagga ggataggtat    1140
gagcgtggac atagaagaca caccacttgg attcagatag tagctctaca atgtaatagt    1200
tgtgtgttca tgtgctacta tttttttttt ttttgagaca gaatctcatt ctgttgccca    1260
ggctggagtg cagtggtgca atcttggctc actgtaacct ccatcacctg ggttcaagcg    1320
attctcgtgc ctccagcctc caagtagctg ggattacag atgtgtgcca ccatacctcg    1380
ctaatctttt tatttttagt agagacagtt tcaccatgtt ggccaggctg gtctccaact    1440
cctgacctca ggtgatcctc ccacctcagc ctcccaaagt gctgggatta caggcatgag    1500
ccaccgcgcc cagccatgca aattctttac tgagtcctgc ctcagtggtc tcctctggaa    1560
aatacgggtg ataactgcac ccacctcaac tggttatcac tgagaagaat aaagaagtta    1620
```

-continued

```
acctgctaaa gcacttaaaa cgttgtttga cacaaagtaa gtgatcaata aattattatt   1680
attattatta ttattattat tattattatt tttgagacag ggtcttgctc tgttgcccag   1740
actggagtgc agtggtgtga tcacagctca ctgcagcttc aacctcttgg gctcaagcaa   1800
ttctcctgcc tcagcctcct gagtagctgg gactacaggc ttgtgccaac atgtctaact   1860
ttttattatt tgtagagaca gggtagtgct gtgttgtcca ggctgttctt gaactcctgg   1920
ttctggtgat cctccagcat gtgcccctgg aagtgctggg attacaggtg tgagacaccg   1980
tgcccggact caatagtcat ttttgagtgc tcatcatgtt ccagacattg ttctaagttt   2040
ttttttttaa tgaatattaa ctccttataa aacttgagaa ggttggagta attatttttt   2100
tccactttgc agaaaagaac attgaggctc caagaagtaa atttacttgc tcacgattag   2160
agaagctgga ttcatgctca gtcagccag ctcccaaatg taccaggtcc tcaattaata    2220
aagagtaagg agaaataaat gacagggctg ggtgcggtgg ctcacgcctg taatcccagc   2280
actttgggtg gctgaggtgg gcacatcact tgaggtcagg agtttgcgac cagcctgaac   2340
aacatggtga accccatctc tataacaata caaaaatcag ccaggcctgc tggcagacac   2400
ctgtaatccc acctactctg gcagagccag aatttgaacc caggactggg tggaataaaa   2460
actctgaact atgtctatga ctgttgtcac aagatcagag ctagactggc caggagccat   2520
gactgtgggt gcagcagcag ctgagccctg atcactaact ctgttcatct tttgcaggag   2580
ataccttccc ggatgcagat gctgatgaag acagtctggc aggcgagctg gatgaggcca   2640
tggggtccag cgagtggctg ccctgacca agtcaccca ggcctttac aggggggcgac     2700 ccagctggca aggaaccct gggttcttc ggggcagccg agatgtcctg gctggccttt     2760
ccagcagctg ctgcaagtgg gggtgtagca aaagtgaaat cagtagcctt gctagtttg    2820 agggctgggc agccgtgggc accaggacca atgccccagt cctgccatcc actcaactag   2880
tgtctggctg ggcacctgtc tttcgagcct cacacattca ttcattcatc tacaagtcac   2940
agaggcactg tgggctcagg cacagtctcc cgacaccacc tatccaaccc tgcccttga    3000 ccagcctatc atgaccctgg cccctaagga agctgtgccc ctgcctggtc aagtggggac   3060 cccccccatcc tgacccctga cctctcccca gccctaacca tgcgtttgcc tggcctacac   3120
actccactgc cacaactggg tccctactct acctaggctg gccacacaga gacccctgcc   3180 ccctttcccag tccaaactgt ggccattgtc ccctgaccag ctaaaatcaa gcctctgtct   3240
cagtccagcc tttgcacgca cgcttccttt gccctgcttt ccatcccctc tccctccaac   3300 tccccctgcca gagttccaag gctgtggacc ccagagaagg tggcaggtgg ccccccagg   3360 agagctctgg gcacattcga atcttcccaa actccaataa taaaaattcg aagactttgg   3420
cagagagtgt gtgtgtgtgt gtatggttg                                     3449
```

<210> SEQ ID NO 7
<211> LENGTH: 72
<212> TYPE: DNA
<213> ORGANISM: Homo sapiens

<400> SEQUENCE: 7

```
gatgtcctgg ctggcctttc cagcagctgc tgcaagtggg ggtgtagcaa aagtgaaatc   60
agtagccttt gc                                                       72
```

<210> SEQ ID NO 8
<211> LENGTH: 81
<212> TYPE: DNA
<213> ORGANISM: Homo sapiens

```
<400> SEQUENCE: 8
cgggcagcgc cttacggggt caggctttgc ggccgagaat tcatccgagc agtcatcttc    60
acctgcgggg gctcccggtg g                                              81

<210> SEQ ID NO 9
<211> LENGTH: 198
<212> TYPE: DNA
<213> ORGANISM: Homo sapiens

<400> SEQUENCE: 9
agacgatcag acatcctggc ccacgaggct atgggagata ccttcccgga tgcagatgct    60
gatgaagaca gtctggcagg cgagctggat gaggccatgg ggtccagcga gtggctggcc   120
ctgaccaagt caccccaggc cttttacagg gggcgaccca gctggcaagg aacccctggg   180
gttcttcggg gcagccga                                                 198

<210> SEQ ID NO 10
<211> LENGTH: 351
<212> TYPE: DNA
<213> ORGANISM: Homo sapiens

<400> SEQUENCE: 10
cgggcagcgc cttacggggt caggctttgc ggccgagaat tcatccgagc agtcatcttc    60
acctgcgggg gctcccggtg gagacgatca gacatcctgg cccacgaggc tatgggagat   120
accttcccgg atgcagatgc tgatgaagac agtctggcag gcgagctgga tgaggccatg   180
gggtccagcg agtggctggc cctgaccaag tcaccccagg ccttttacag ggggcgaccc   240
agctggcaag gaacccctgg ggttcttcgg ggcagccgag atgtcctggc tggccttttcc  300 agcagctgct gcaagtgggg gtgtagcaaa agtgaaatca gtagcctttg c            351

<210> SEQ ID NO 11
<211> LENGTH: 21
<212> TYPE: DNA
<213> ORGANISM: Artificial Sequence
<220> FEATURE:
<223> OTHER INFORMATION: M3 relaxin Forward primer

<400> SEQUENCE: 11
tgcggaggct cacgatggcg c                                              21

<210> SEQ ID NO 12
<211> LENGTH: 21
<212> TYPE: DNA
<213> ORGANISM: Artificial Sequence
<220> FEATURE:
<223> OTHER INFORMATION: M3 relaxin Reverse primer

<400> SEQUENCE: 12
gacagcagct tgcaggcacg g                                              21

<210> SEQ ID NO 13
<211> LENGTH: 23
<212> TYPE: DNA
<213> ORGANISM: Artificial Sequence
<220> FEATURE:
<223> OTHER INFORMATION: M1 relaxin forward primer

<400> SEQUENCE: 13
gtgaatatgc ccgtgaattg atc                                            23
```

```
<210> SEQ ID NO 14
<211> LENGTH: 21
<212> TYPE: DNA
<213> ORGANISM: Artificial Sequence
<220> FEATURE:
<223> OTHER INFORMATION: M1 relaxin reverse primer

<400> SEQUENCE: 14
agcgtcgtat cgaaaggctc t                                            21

<210> SEQ ID NO 15
<211> LENGTH: 21
<212> TYPE: DNA
<213> ORGANISM: Artificial Sequence
<220> FEATURE:
<223> OTHER INFORMATION: H3 relaxin forward primer 1

<400> SEQUENCE: 15
acgttcaaag cgtctccgtc c                                            21

<210> SEQ ID NO 16
<211> LENGTH: 21
<212> TYPE: DNA
<213> ORGANISM: Artificial Sequence
<220> FEATURE:
<223> OTHER INFORMATION: H3 relaxin forward primer 2

<400> SEQUENCE: 16
cggtggagac gatcagacat c                                            21

<210> SEQ ID NO 17
<211> LENGTH: 21
<212> TYPE: DNA
<213> ORGANISM: Artificial Sequence
<220> FEATURE:
<223> OTHER INFORMATION: H3 relaxin reverse primer

<400> SEQUENCE: 17
atggcaggac tggggcattg g                                            21

<210> SEQ ID NO 18
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 18
tgatgacatc aagaaggtgg                                              20

<210> SEQ ID NO 19
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 19
tttcttactc cttggaggcc                                              20

<210> SEQ ID NO 20
<211> LENGTH: 21
<212> TYPE: DNA
<213> ORGANISM: Artificial Sequence
<220> FEATURE:
<223> OTHER INFORMATION: M3 forward primer 2
```

<400> SEQUENCE: 20
gggtcgcagg catctcaact g                                              21

<210> SEQ ID NO 21
<211> LENGTH: 21
<212> TYPE: DNA
<213> ORGANISM: Artificial Sequence
<220> FEATURE:
<223> OTHER INFORMATION: H3 relaxin exon II forward primer

<400> SEQUENCE: 21
cggatgcaga tgctgatgaa g                                              21

<210> SEQ ID NO 22
<211> LENGTH: 21
<212> TYPE: DNA
<213> ORGANISM: Artificial Sequence
<220> FEATURE:
<223> OTHER INFORMATION: H3 relaxin exon II reverse primer

<400> SEQUENCE: 22
gtgcctgagc ccacagtgcc t                                              21

<210> SEQ ID NO 23
<211> LENGTH: 39
<212> TYPE: DNA
<213> ORGANISM: Artificial Sequence
<220> FEATURE:
<223> OTHER INFORMATION: M1 relaxin internal probe

<400> SEQUENCE: 23
caagcagagc tggctcctcc tggctcaaag ccaatcttc                           39

<210> SEQ ID NO 24
<211> LENGTH: 39
<212> TYPE: DNA
<213> ORGANISM: Artificial Sequence
<220> FEATURE:
<223> OTHER INFORMATION: M3 relaxin internal probe

<400> SEQUENCE: 24
aatttggctc ttgctacagc cccactcgca gcaactgct                           39

<210> SEQ ID NO 25
<211> LENGTH: 78
<212> TYPE: DNA
<213> ORGANISM: Artificial Sequence
<220> FEATURE:
<223> OTHER INFORMATION: M3 relaxin mRNA sequence probe 1

<400> SEQUENCE: 25
ggtggtctgt attggcttct ccatcagcga agaagtcccg gtggtctgta ttggcttctc    60
catcagcgaa gaagtccc                                                  78

<210> SEQ ID NO 26
<211> LENGTH: 39
<212> TYPE: DNA
<213> ORGANISM: Artificial Sequence
<220> FEATURE:
<223> OTHER INFORMATION: M3 relaxin mRNA sequence probe 2

<400> SEQUENCE: 26
aatttggctc ttgctacagc cccactcgca cgaactgct                           39

```
<210> SEQ ID NO 27
<211> LENGTH: 39
<212> TYPE: DNA
<213> ORGANISM: Artificial Sequence
<220> FEATURE:
<223> OTHER INFORMATION: M3 relaxin mRNA sequence probe 3

<400> SEQUENCE: 27
taaggagaca gtggacccct tggtgcctcg cctgtagga                              39

<210> SEQ ID NO 28
<211> LENGTH: 39
<212> TYPE: DNA
<213> ORGANISM: Artificial Sequence
<220> FEATURE:
<223> OTHER INFORMATION: M1 relaxin mRNA sequence probe 1

<400> SEQUENCE: 28
gcacatccga atgaatccgt ccatccactc ctccgagac                              39

<210> SEQ ID NO 29
<211> LENGTH: 39
<212> TYPE: DNA
<213> ORGANISM: Artificial Sequence
<220> FEATURE:
<223> OTHER INFORMATION: M1 relaxin mRNA sequence probe 2

<400> SEQUENCE: 29
caagcagagc tggctcctcc tggctcaaag ccaatcttc                              39

<210> SEQ ID NO 30
<211> LENGTH: 39
<212> TYPE: DNA
<213> ORGANISM: Artificial Sequence
<220> FEATURE:
<223> OTHER INFORMATION: M1 relaxin mRNA sequence probe 3

<400> SEQUENCE: 30
gttgtagctc tgggagcgag gcctgagcct cagacagta                              39

<210> SEQ ID NO 31
<211> LENGTH: 8
<212> TYPE: PRT
<213> ORGANISM: Artificial Sequence
<220> FEATURE:
<223> OTHER INFORMATION: relaxin receptor consensus binding domain
<220> FEATURE:
<221> NAME/KEY: MISC_FEATURE
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (6)..(7)
<223> OTHER INFORMATION: Xaa can be any naturally occurring amino acid

<400> SEQUENCE: 31

Arg Xaa Xaa Xaa Arg Xaa Xaa Ile
1               5

<210> SEQ ID NO 32
<211> LENGTH: 1194
<212> TYPE: DNA
<213> ORGANISM: Homo sapiens

<400> SEQUENCE: 32
tataaatggg gggccaagag gcagcagaga cactggccca ctctcacgtt caaagcgtct       60
ccgtccagca tggccaggta catgctgctg ctgctcctgg cggtatgggt gctgaccggg      120
```

| | | |
|---|---|---|
| gagctgtggc cgggagctga ggcccgggca gcgccttacg gggtcaggct ttgcggccga | 180 | |
| gaattcatcc gagcagtcat cttcacctgc gggggctccc ggtggagacg atcagacatc | 240 | |
| ctggcccacg aggctatggg tgaggctggg gagagagtgg atgtagaagg ggaacagcac | 300 | |
| taactctgtt catcttttgc aggagatacc ttcccggatg cagatgctga tgaagacagt | 360 | |
| ctggcaggcg agctggatga ggccatgggg tccagcgagt ggctggccct gaccaagtca | 420 | |
| ccccaggcct tttacagggg gcgacccagc tggcaaggaa cccctggggt tcttcggggc | 480 | |
| agccgagatg tcctggctgg ccttttccagc agctgctgca agtggggtg tagcaaaagt | 540 | |
| gaaatcagta gcctttgcta gtttgagggc tgggcagccg tgggcaccag gaccaatgcc | 600 | |
| ccagtcctgc catccactca actagtgtct ggctgggcac ctgtctttcg agcctcacac | 660 | |
| attcattcat tcatctacaa gtcacagagg cactgtgggc tcaggcacag tctcccgaca | 720 | |
| ccacctatcc aaccctgccc tttgaccagc ctatcatgac cctggcccct aaggaagctg | 780 | |
| tgcccctgcc tggtcaagtg ggacccccc catcctgacc cctgacctct ccccagccct | 840 | |
| aaccatgcgt ttgcctggcc tacacactcc actgccacaa ctgggtccct actctaccta | 900 | |
| ggctggccac acagagaccc ctgccccctt cccagtccaa actgtggcca ttgtcccctg | 960 | |
| accagctaaa atcaagcctc tgtctcagtc cagcctttgc acgcacgctt cctttgccct | 1020 | |
| gctttccatc ccctctccct ccaactcccc tgccagagtt ccaaggctgt ggaccccaga | 1080 | |
| gaaggtggca ggtggccccc ctaggagagc tctgggcaca ttcgaatctt cccaaaactcc | 1140 | |
| aataataaaa attcgaagac tttggcagag agtgtgtgtg tgtgtgtatg gttg | 1194 | |

<210> SEQ ID NO 33
<211> LENGTH: 1013
<212> TYPE: DNA
<213> ORGANISM: Homo sapiens

<400> SEQUENCE: 33

| | | |
|---|---|---|
| tataaatagg ggatcggagg tggtgcagat agagcacctg ggtcgcaggc atctcaactg | 60 | |
| atcatggcaa tgctcgggct gctgctgctg gcttcctggg ctctcctcgg ggctctgggg | 120 | |
| ctgcaggccg aggcgaggcc ggcgcccctac ggggtgaagc tctgcggtcg ggagttcatc | 180 | |
| cgcgcggtca tcttcacttg cggaggctca cgatggcgcc gggcggacat cttggcccac | 240 | |
| gaatctctgg gtgagtgcta ggcaatcaac ctggaacagg tgtcctggta agcgcaactt | 300 | |
| ttgcagggga cttcttcgct gatggagaag ccaatacaga ccacctggcc agcgagctgg | 360 | |
| atgaagcggt gggctccagc gagtggctgg ccctaaccaa atcccccag gctttctacg | 420 | |
| gtggtcgagc cagctggcaa gggtcacctg gagtggttcg gggcagcaga gatgtgttgg | 480 | |
| ctggcctttc cagcagttgc tgcgagtggg gctgtagcaa gagccaaatt agcagcttgt | 540 | |
| gctaggatca gggttgagca atggagaagc gggccgtgcc tgcaagctgc tgtcagctgt | 600 | |
| gcgatgttca agagcattcc tacaggcgag gcaccaaggg gtccactgtc tccttacaga | 660 | |
| ccctctgcca agatgcacac actacgtgcc aaccttttccc caccttgctg ccggcccctc | 720 | |
| ctctatccag ccaaacagaa acttgttttt catgactgag ttcttccgtg ccacaacctc | 780 | |
| accccccagca gcccagcagc aaccagatgc ccatcttctt aaactggcta cactagagtc | 840 | |
| tgccccacct ccaccctcag tccggcccta attgccgcca ctgtccctgg ctaacctgcc | 900 | |
| ccccccccaa aaaaaaaaa acagagcact ctgttgcaga ccccaggact gagggcccct | 960 | |
| ggtcctcagt actcagactt cctcaccaca taaaataaag gttcagttct gag | 1013 | |

```
<210> SEQ ID NO 34
<211> LENGTH: 28
<212> TYPE: PRT
<213> ORGANISM: Homo sapiens

<400> SEQUENCE: 34

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 35
<211> LENGTH: 29
<212> TYPE: PRT
<213> ORGANISM: Homo sapiens

<400> SEQUENCE: 35

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 36
<211> LENGTH: 5
<212> TYPE: PRT
<213> ORGANISM: Artificial Sequence
<220> FEATURE:
<223> OTHER INFORMATION: Relaxin consensus sequence

<400> SEQUENCE: 36

Leu Cys Gly Arg Glu
1               5

<210> SEQ ID NO 37
<211> LENGTH: 13
<212> TYPE: PRT
<213> ORGANISM: Homo sapiens

<400> SEQUENCE: 37

Cys Gly Arg Glu Phe Ile Arg Ala Val Ile Phe Thr Cys
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Relaxin consensus sequence

<400> SEQUENCE: 38

Ala Pro Tyr Gly Val
1               5

<210> SEQ ID NO 39
<211> LENGTH: 19
<212> TYPE: PRT
<213> ORGANISM: Artificial Sequence
<220> FEATURE:
<223> OTHER INFORMATION: Relaxin consensus sequence

<400> SEQUENCE: 39

Leu Cys Gly Arg Glu Phe Ile Arg Ala Val Ile Phe Thr Cys Gly Gly
1               5                   10                  15

Ser Arg Trp
```

```
<210> SEQ ID NO 40
<211> LENGTH: 27
<212> TYPE: PRT
<213> ORGANISM: Mus musculus

<400> SEQUENCE: 40

Arg Pro Ala Pro Tyr Gly Val Lys Leu Cys Gly Arg Glu Phe Ile Arg
1               5                   10                  15

Ala Val Ile Phe Thr Cys Gly Gly Ser Arg Trp
            20                  25

<210> SEQ ID NO 41
<211> LENGTH: 4
<212> TYPE: PRT
<213> ORGANISM: Artificial Sequence
<220> FEATURE:
<223> OTHER INFORMATION: Relaxin consensus sequence

<400> SEQUENCE: 41

Cys Gly Arg Glu
1

<210> SEQ ID NO 42
<211> LENGTH: 35
<212> TYPE: PRT
<213> ORGANISM: Mus musculus

<400> SEQUENCE: 42

Arg Val Ser Glu Glu Trp Met Asp Gly Phe Ile Arg Met Cys Gly Arg
1               5                   10                  15

Glu Tyr Ala Arg Glu Leu Ile Lys Ile Cys Gly Ala Ser Val Gly Arg
            20                  25                  30

Leu Ala Leu
        35

<210> SEQ ID NO 43
<211> LENGTH: 24
<212> TYPE: PRT
<213> ORGANISM: Homo sapiens

<400> SEQUENCE: 43

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 44
<211> LENGTH: 24
<212> TYPE: PRT
<213> ORGANISM: Homo sapiens

<400> SEQUENCE: 44

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 45
<211> LENGTH: 15
<212> TYPE: PRT
<213> ORGANISM: Homo sapiens
```

```
<220> FEATURE:
<221> NAME/KEY: MISC_FEATURE
<222> LOCATION: (3)..(3)
<223> OTHER INFORMATION: Xaa is Glu or Lys
<220> FEATURE:
<221> NAME/KEY: MISC_FEATURE
<222> LOCATION: (10)..(10)
<223> OTHER INFORMATION: Xaa is Gln or Glu

<400> SEQUENCE: 45

Cys Cys Xaa Trp Gly Cys Ser Lys Ser Xaa Ile Ser Ser Leu Cys
1               5                   10                  15

<210> SEQ ID NO 46
<211> LENGTH: 11
<212> TYPE: PRT
<213> ORGANISM: Artificial Sequence
<220> FEATURE:
<223> OTHER INFORMATION: Relaxin consensus sequence

<400> SEQUENCE: 46

Asp Val Leu Ala Gly Leu Ser Ser Ser Cys Cys
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Relaxin consensus sequence

<400> SEQUENCE: 47

Trp Gly Cys Ser Lys Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Relaxin consensus sequence

<400> SEQUENCE: 48

Ile Ser Ser Leu Cys
1               5

<210> SEQ ID NO 49
<211> LENGTH: 24
<212> TYPE: PRT
<213> ORGANISM: Rattus norvegicus

<400> SEQUENCE: 49

Asp Val Leu Ala Gly Leu Ser Ser Ser Cys Cys Glu Trp Gly Cys Ser
1               5                   10                  15

Lys Ser Gln Ile Ser Ser Leu Cys
            20

<210> SEQ ID NO 50
<211> LENGTH: 24
<212> TYPE: PRT
<213> ORGANISM: Mus musculus
```

```
<400> SEQUENCE: 50

Asp Val Leu Ala Gly Leu Ser Ser Ser Cys Cys Glu Trp Gly Cys Ser
1               5                   10                  15

Lys Ser Gln Ile Ser Ser Leu Cys
            20

<210> SEQ ID NO 51
<211> LENGTH: 25
<212> TYPE: PRT
<213> ORGANISM: Mus musculus

<400> SEQUENCE: 51

Glu Ser Gly Gly Leu Met Ser Gln Gln Cys Cys His Val Gly Cys Ser
1               5                   10                  15

Arg Arg Ser Ile Ala Lys Leu Tyr Cys
            20                  25

<210> SEQ ID NO 52
<211> LENGTH: 1194
<212> TYPE: DNA
<213> ORGANISM: Artificial Sequence
<220> FEATURE:
<223> OTHER INFORMATION: H3 relaxin assembled gene sequence

<400> SEQUENCE: 52
tataaatggg gggccaagag gcagcagaga cactggccca ctctcacgtt caaagcgtct      60
ccgtccagca tggccaggta catgctgctg ctgctcctgg cggtatgggt gctgaccggg     120
gagctgtggc cgggagctga ggcccgggca gcgccttacg gggtcaggct ttgcggccga     180
gaattcatcc gagcagtcat cttcacctgc gggggctccc ggtggagacg atcagacatc     240
ctggcccacg aggctatggg tgaggctggg gagagagtgg atgtagaagg ggaacagcac     300
taactctgtt catcttttgc aggagatacc ttcccggatg cagatgctga tgaagacagt     360
ctggcaggcg agctggatga ggccatgggg tccagcgagt ggctggccct gaccaagtca     420
ccccaggcct tttacagggg gcgacccagc tggcaaggaa cccctggggt tcttcgggcc     480
agccgagatg tcctggctgg ccttttccagc agctgctgca gtgggggtg tagcaaaagt    540
gaaatcagta gcctttgcta gtttgagggc tgggcagccg tgggcaccag gaccaatgcc     600
ccagtcctgc catccactca actagtgtct ggctgggcac ctgtctttcg agcctcacac     660
attcattcat tcatctacaa gtcacagagg cactgtgggc tcaggcacag tctcccgaca     720
ccacctatcc aaccctgccc tttgaccagc ctatcatgac cctggcccct aaggaagctg     780
tgcccctgcc tggtcaagtg ggacccccc catcctgacc cctgacctct ccccagccct      840
aaccatgcgt ttgcctggcc tacacactcc actgccacaa ctgggtccct actctaccta     900
ggctggccac acagagaccc ctgccccctt cccagtccaa actgtggcca ttgtcccctg     960
accagctaaa atcaagcctc tgtctcagtc cagcctttgc acgcacgctt cctttgccct    1020
gctttccatc ccctctccct ccaactcccc tgccagagtt ccaaggctgt ggaccccaga    1080
gaaggtggca ggtggccccc ctaggagagc tctgggcaca ttcgaatctt cccaaactcc    1140
aataataaaa attcgaagac tttggcagag agtgtgtgtg tgtgtgtatg gttg          1194

<210> SEQ ID NO 53
<211> LENGTH: 142
<212> TYPE: PRT
<213> ORGANISM: Artificial Sequence
<220> FEATURE:
<223> OTHER INFORMATION: H3 relaxin assembled protein
```

<400> SEQUENCE: 53

```
Met Ala Arg Tyr Met Leu Leu Leu Leu Ala Val Trp Val Leu Thr
1               5                   10                  15

Gly Glu Leu Trp Pro Gly Ala Glu Ala Arg Ala Pro Tyr Gly Val
            20                  25                  30

Arg Leu Cys Gly Arg Glu Phe Ile Arg Ala Val Ile Phe Thr Cys Gly
        35                  40                  45

Gly Ser Arg Trp Arg Arg Ser Asp Ile Leu Ala His Glu Ala Met Gly
    50                  55                  60

Asp Thr Phe Pro Asp Ala Asp Ala Asp Glu Asp Ser Leu Ala Gly Glu
65                  70                  75                  80

Leu Asp Glu Ala Met Gly Ser Ser Glu Trp Leu Ala Leu Thr Lys Ser
                85                  90                  95

Pro Gln Ala Phe Tyr Arg Gly Arg Pro Ser Trp Gln Thr Pro Gly
            100                 105                 110

Val Leu Arg Gly Ser Arg Asp Val Leu Ala Gly Leu Ser Ser Ser Cys
            115                 120                 125

Cys Lys Trp Gly Cys Ser Lys Ser Glu Ile Ser Ser Leu Cys
130                 135                 140
```

<210> SEQ ID NO 54
<211> LENGTH: 1013
<212> TYPE: DNA
<213> ORGANISM: Artificial Sequence
<220> FEATURE:
<223> OTHER INFORMATION: M3 relaxin assembled gene sequence

<400> SEQUENCE: 54

```
tataaatagg ggatcggagg tggtgcagat agagcacctg ggtcgcaggc atctcaactg      60
atcatggcaa tgctcgggct gctgctgctg gcttcctggg ctctcctcgg ggctctgggg     120
ctgcaggccg aggcgaggcc ggcgccctac ggggtgaagc tctgcggtcg ggagttcatc     180
cgcgcggtca tcttcacttg cggaggctca cgatggcgcc gggcggacat cttggcccac     240
gaatctctgg gtgagtgcta ggcaatcaac ctggaacagg tgtcctggta agcgcaactt     300
ttgcagggga cttcttcgct gatggagaag ccaatacaga ccacctggcc agcgagctgg     360
atgaagcggt gggctccagc gagtggctgg ccctaaccaa atcccccag gctttctacg      420
gtggtcgagc cagctggcaa gggtcacctg agtggttcg gggcagcaga gatgtgttgg      480
ctggcctttc cagcagttgc tgcgagtggg gctgtagcaa gagccaaatt agcagcttgt     540
gctaggatca gggttgagca atggagaagc gggccgtgcc tgcaagctgc tgtcagctgt     600
gcgatgttca agagcattcc tacaggcgag gcaccaaggg gtccactgtc tccttacaga     660
ccctctgcca agatgcacac actacgtgcc aacctttccc caccttgctg ccggccctc      720
ctctatccag ccaaacagaa acttgttttt catgactgag ttcttccgtg ccacaacctc     780
accccccagca gcccagcagc aaccagatgc ccatcttctt aaactggcta cactagagtc    840
tgccccacct ccaccctcag tccggcccta attgccgcca ctgtccctgg ctaacctgcc     900
cccccccaa aaaaaaaaaa acagagcact ctgttgcaga ccccaggact gagggcccct      960
ggtcctcagt actcagactt cctcaccaca taaaataaag gttcagttct gag           1013
```

<210> SEQ ID NO 55
<211> LENGTH: 141
<212> TYPE: PRT
<213> ORGANISM: Artificial Sequence

```
<220> FEATURE:
<223> OTHER INFORMATION: M3 relaxin assembled protein

<400> SEQUENCE: 55

Met Ala Met Leu Gly Leu Leu Leu Ala Ser Trp Ala Leu Leu Gly
1               5                   10                  15

Ala Leu Gly Leu Gln Ala Glu Ala Arg Pro Ala Pro Tyr Gly Val Lys
            20                  25                  30

Leu Cys Gly Arg Glu Phe Ile Arg Ala Val Ile Phe Thr Cys Gly Gly
        35                  40                  45

Ser Arg Trp Arg Arg Ala Asp Ile Leu Ala His Glu Ser Leu Gly Asp
    50                  55                  60

Phe Phe Ala Asp Gly Glu Ala Asn Thr Asp His Leu Ala Ser Glu Leu
65                  70                  75                  80

Asp Glu Ala Val Gly Ser Ser Glu Trp Leu Ala Leu Thr Lys Ser Pro
                85                  90                  95

Gln Ala Phe Tyr Gly Gly Arg Ala Ser Trp Gln Gly Ser Pro Gly Val
            100                 105                 110

Val Arg Gly Ser Arg Asp Val Leu Ala Gly Leu Ser Ser Ser Cys Cys
        115                 120                 125

Glu Trp Gly Cys Ser Lys Ser Gln Ile Ser Ser Leu Cys
    130                 135                 140

<210> SEQ ID NO 56
<211> LENGTH: 27
<212> TYPE: PRT
<213> ORGANISM: Artificial Sequence
<220> FEATURE:
<223> OTHER INFORMATION: Human 3 B chain

<400> SEQUENCE: 56

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 57
<211> LENGTH: 24
<212> TYPE: PRT
<213> ORGANISM: Artificial Sequence
<220> FEATURE:
<223> OTHER INFORMATION: Human 3 A chain

<400> SEQUENCE: 57

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 58
<211> LENGTH: 39
<212> TYPE: DNA
<213> ORGANISM: Artificial Sequence
<220> FEATURE:
<223> OTHER INFORMATION: mRNA oligonucleotide

<400> SEQUENCE: 58
ggtggtctgt attggcttct ccatcagcga agaagtccc                    39
```